(12) United States Patent
Cho et al.

(10) Patent No.: US 10,272,049 B2
(45) Date of Patent: Apr. 30, 2019

(54) GENE CARRIER USING CELL-DERIVED NANOVESICLES AND METHOD FOR PREPARING THE SAME

(71) Applicant: UNIVERSITY-INDUSTRY FOUNDATION, YONSEI UNIVERSITY, Seoul (KR)

(72) Inventors: Seung-Woo Cho, Seoul (KR); Yoon Hee Jin, Seoul (KR)

(73) Assignee: University-Industry Foundation, Yonsei University (KR)

( * ) Notice: Subject to any disclaimer, the term of this patent is extended or adjusted under 35 U.S.C. 154(b) by 11 days.

(21) Appl. No.: 15/495,395

(22) Filed: Apr. 24, 2017

(65) Prior Publication Data

US 2017/0304212 A1 Oct. 26, 2017

(30) Foreign Application Priority Data

Apr. 25, 2016 (KR) .......................... 10-2016-0049854

(51) Int. Cl.

| A61K 9/51 | (2006.01) |
|---|---|
| A61K 31/713 | (2006.01) |
| A61K 48/00 | (2006.01) |
| C12N 15/11 | (2006.01) |
| C12N 15/88 | (2006.01) |
| A61K 9/50 | (2006.01) |

(52) U.S. Cl.
CPC .............. *A61K 9/51* (2013.01); *A61K 9/5192* (2013.01); *A61K 31/713* (2013.01); *A61K 48/005* (2013.01); *C12N 15/111* (2013.01); *C12N 15/88* (2013.01); *A61K 9/5068* (2013.01); *C12N 2320/32* (2013.01)

(58) Field of Classification Search
None
See application file for complete search history.

(56) References Cited

PUBLICATIONS

Kim, et al. (2014) "Large-scale generation of cell-derived nanovesicles", Nanoscale, 6: 12056-64.*
Ohno, et al. (2013) "Systemically injected exosomes targeted to EGFR deliver antitumor microRNA to breast cancer cells", Molecular Therapy, 21(1): 185-91.*
Lamichhane et al., "Exogenous DNA Loading into Extracellular Vesicles via Electroporation is Size-Dependent and Enables Limited Gene Delivery", Mol. Pharmaceutics, 2015, v. 12:3650-3657.
Office Action for Application No. KR 10-2016-0049854 with brief translation dated Jul. 26, 2017, 6 pages.
Yoon et al., "Generation of nanovesicles with sliced cellular membrane fragments for exogenous material delivery", Biomaterials, 2015, v. 59:12-20.

* cited by examiner

*Primary Examiner* — Robert M Kelly
(74) *Attorney, Agent, or Firm* — Adsero IP

(57) ABSTRACT

Provided are a gene carrier using cell-derived nanovesicles and a method for preparing the same. The gene carrier prepared by inserting a gene into the nanovesicles artificially outbudded from a plasma membrane has excellent delivery efficiency to a target organ and cells, induces long-term regulation of gene expression, and facilitates mass production due to a simple preparation process, and thus can be used as a core technique for the gene or cell therapeutic agent field.

10 Claims, 32 Drawing Sheets

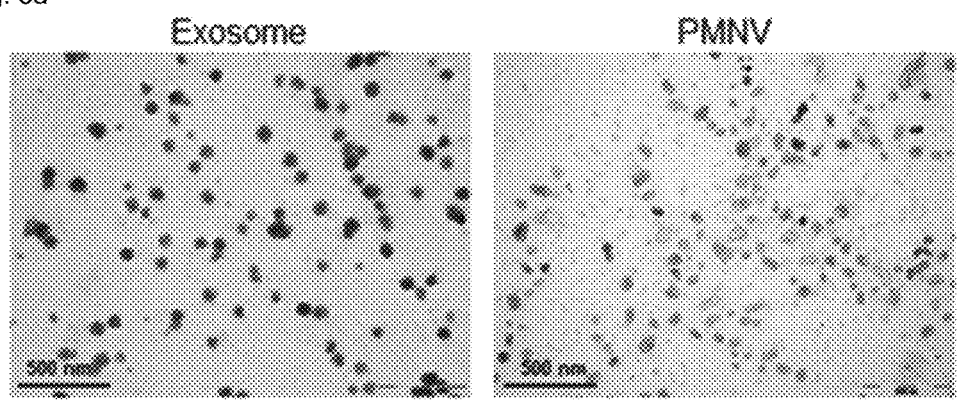
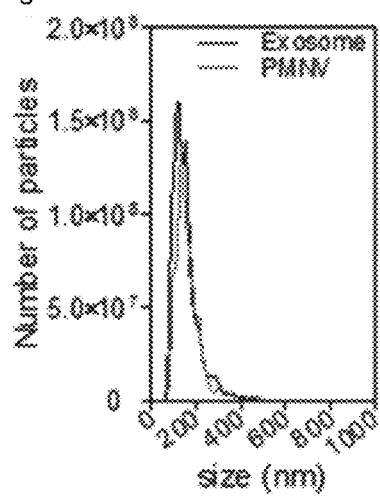
Fig. 3a
Exosome    PMNV
Fig. 3b

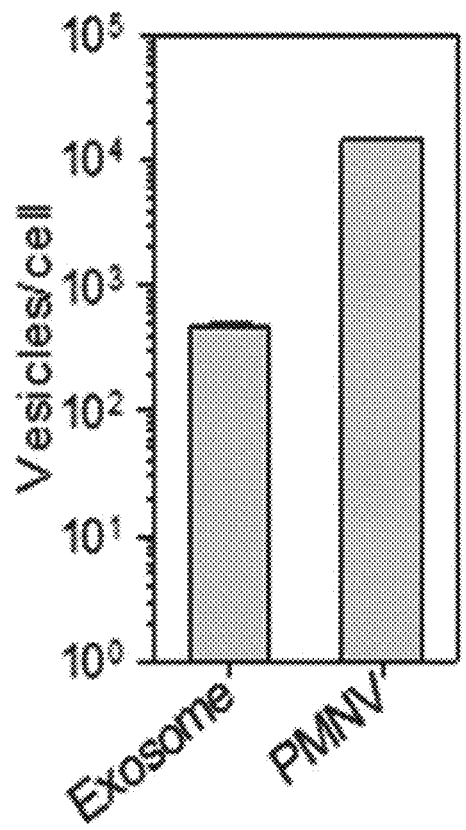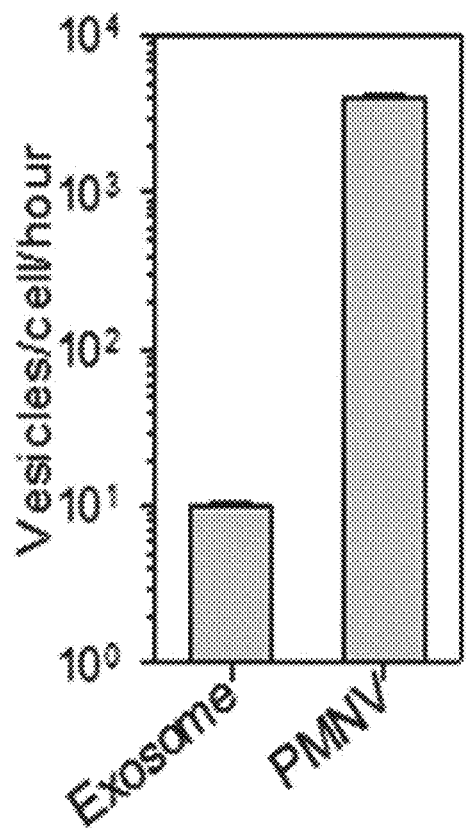

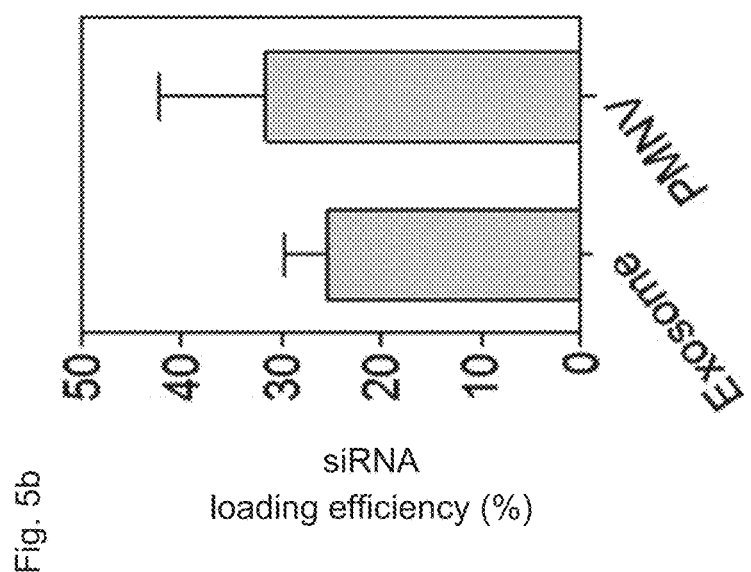
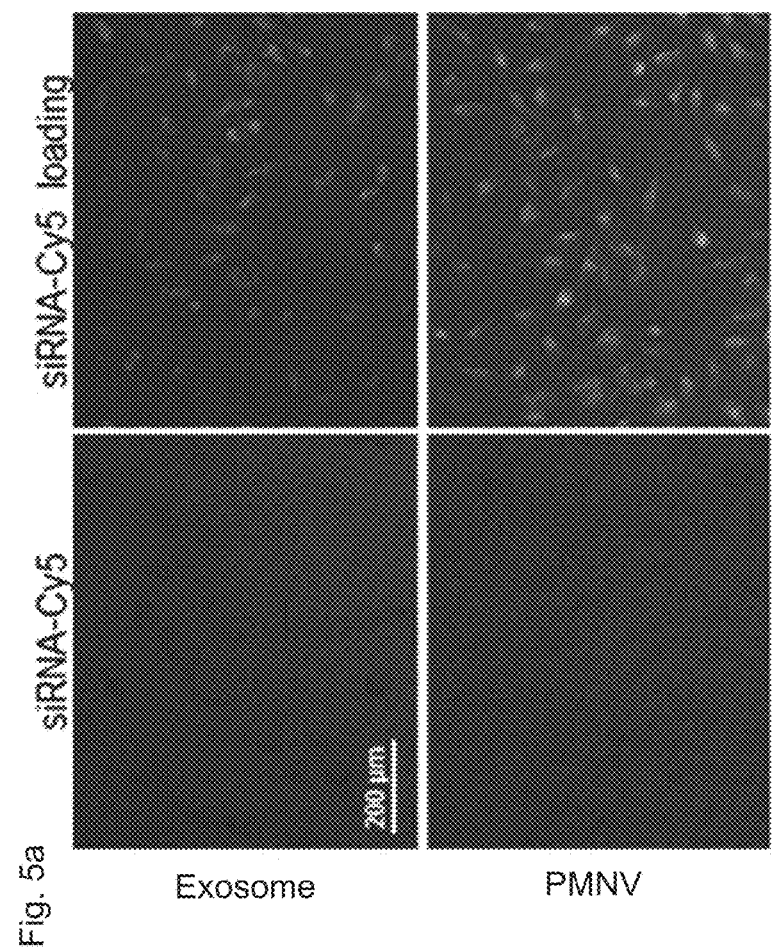
Fig. 5b
Fig. 5a

EGFP-HeLa

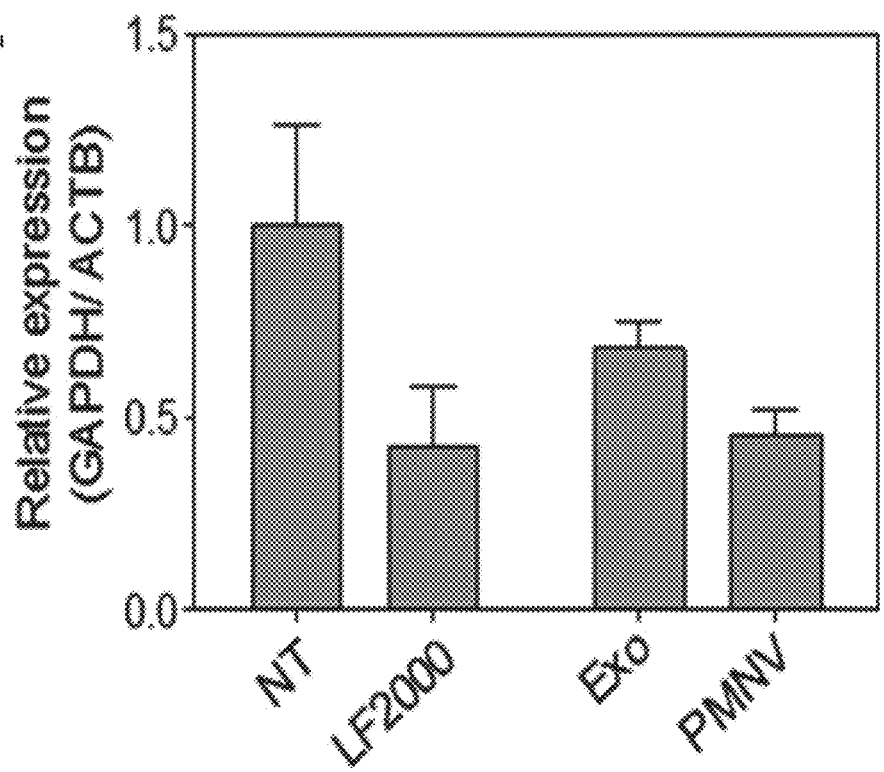

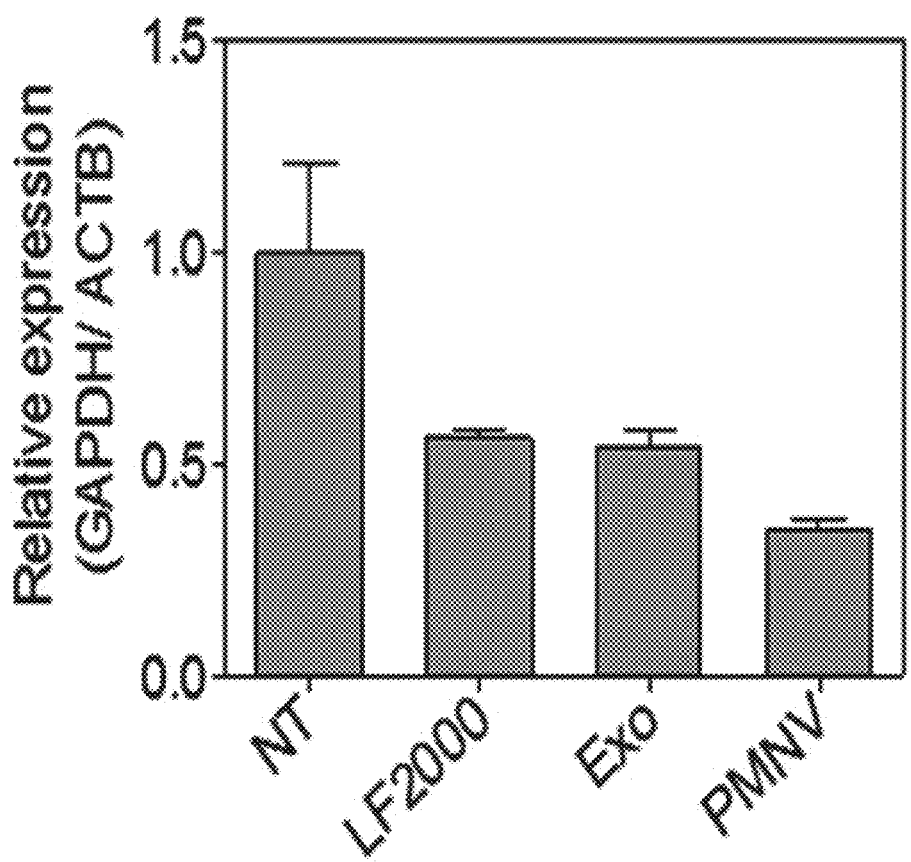

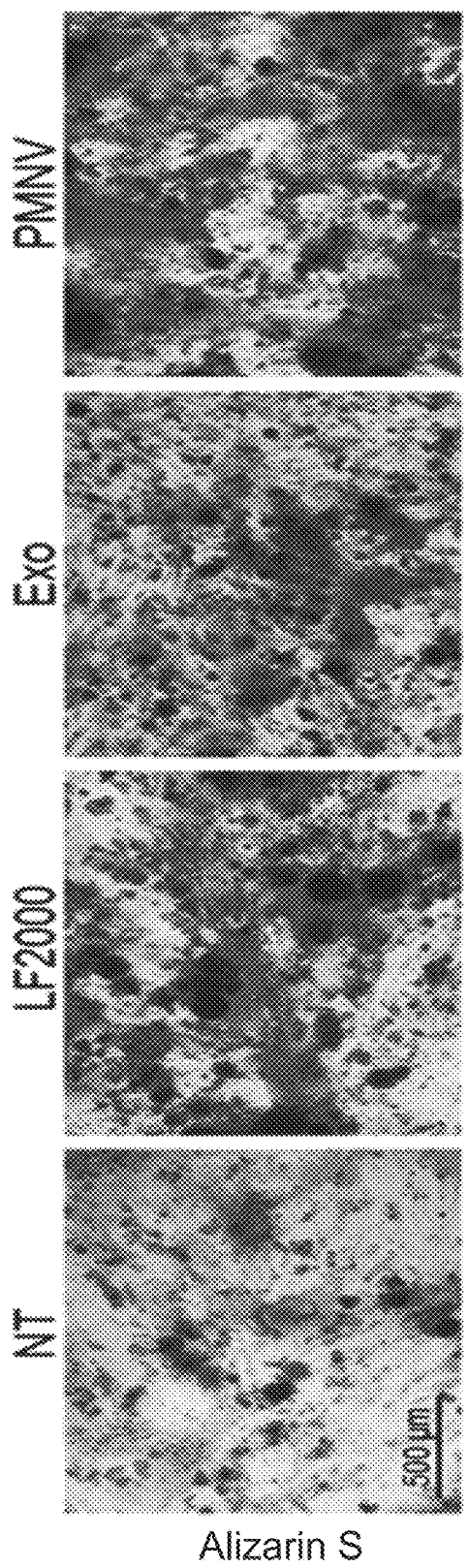

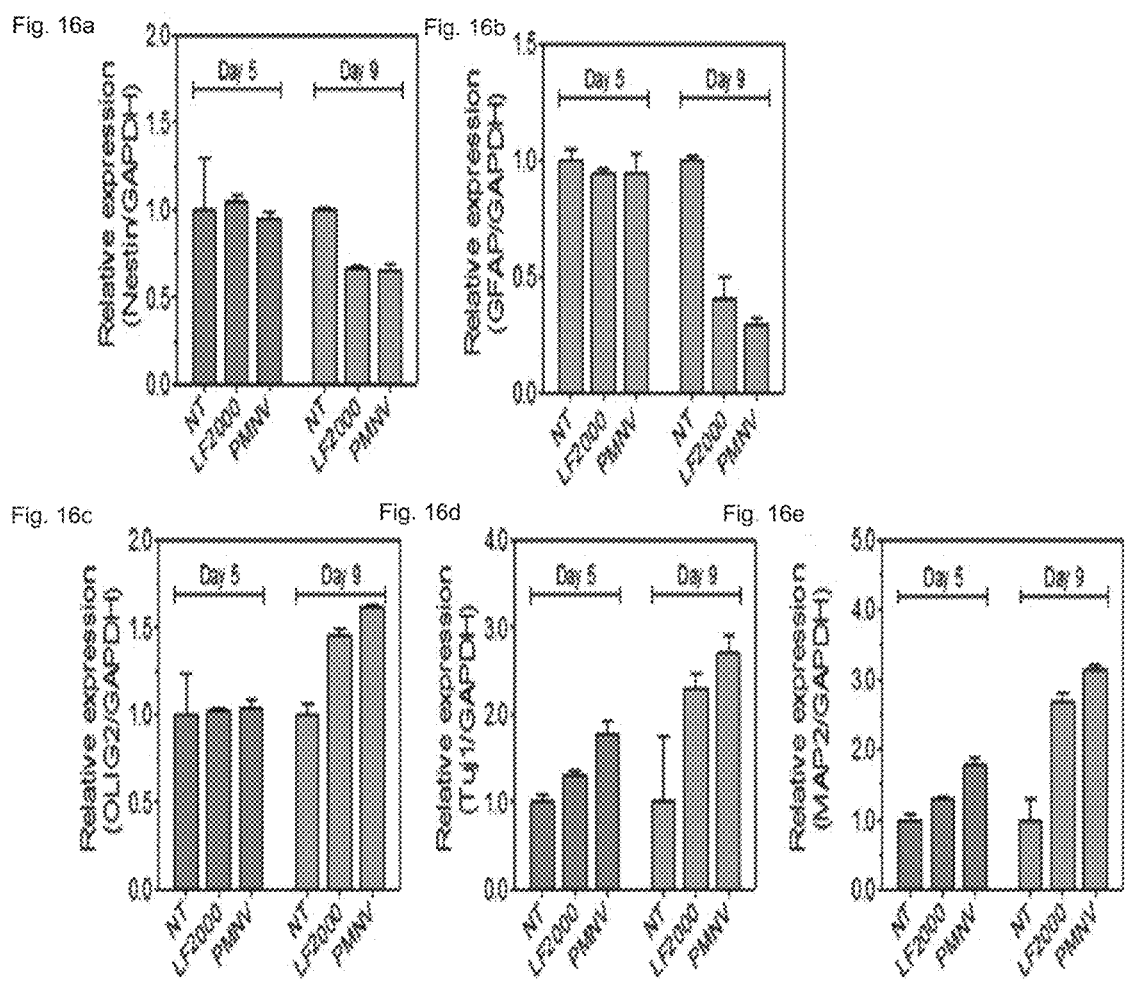

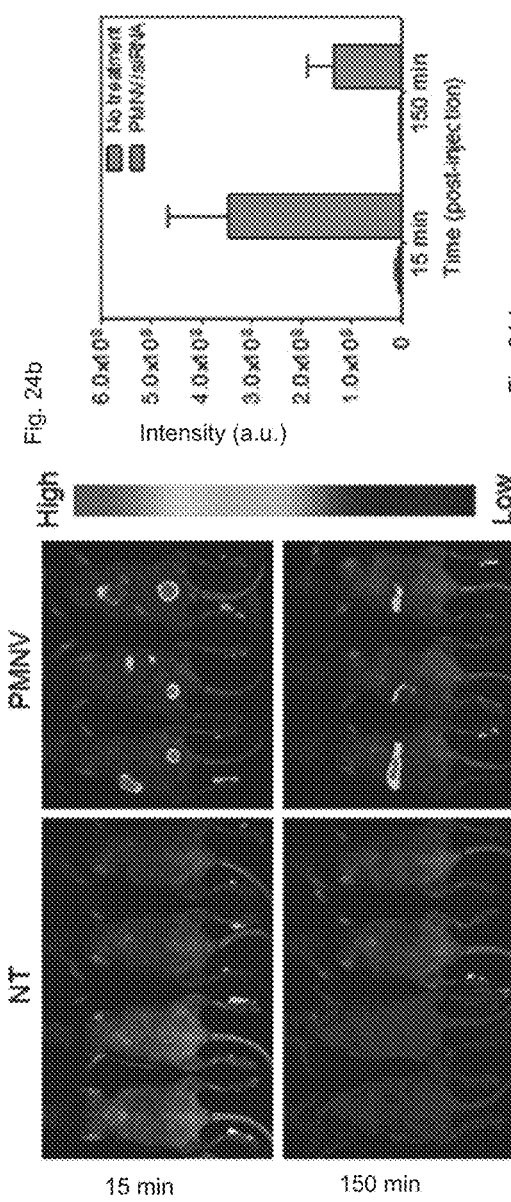
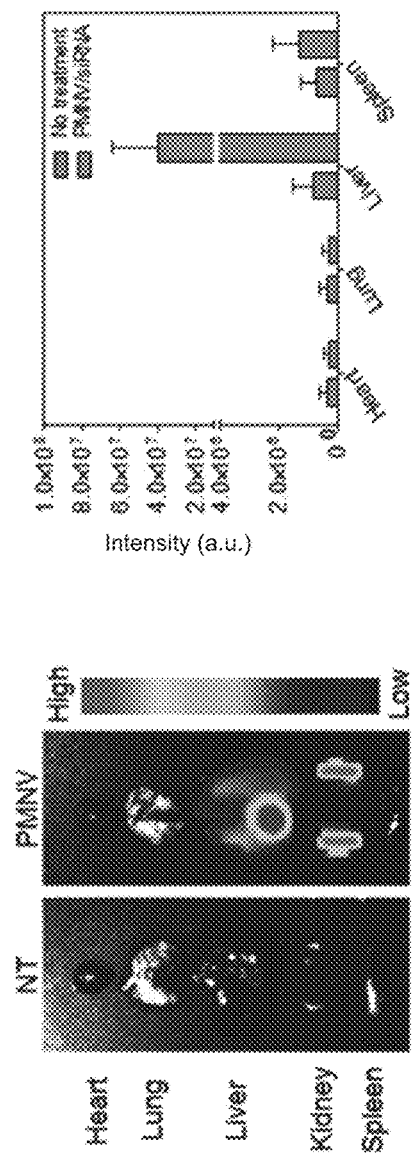
Fig. 24a
Fig. 24b
Fig. 24c
Fig. 24d

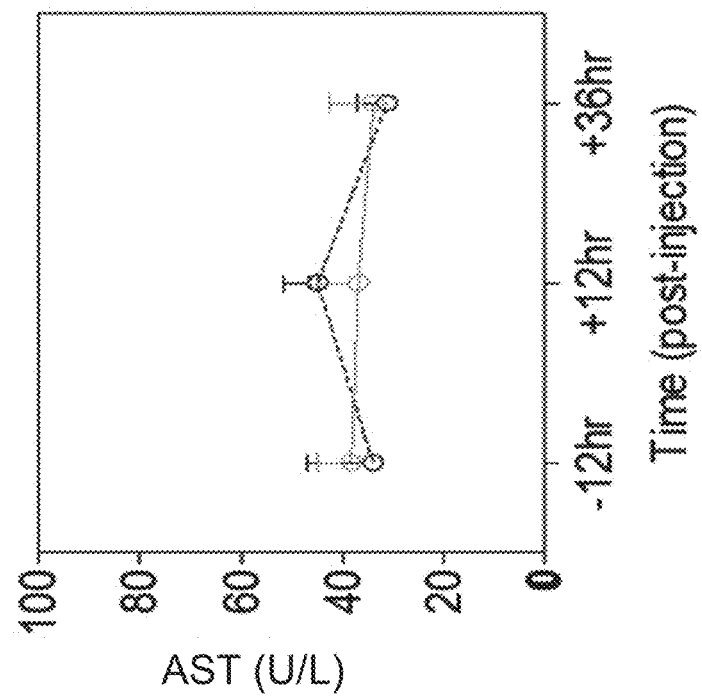
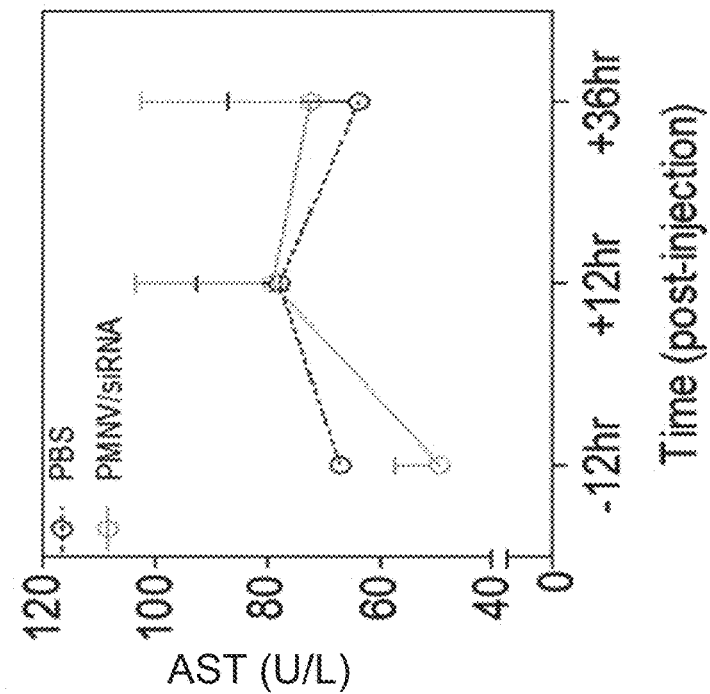
Fig. 26a
Fig. 26b

GENE CARRIER USING CELL-DERIVED NANOVESICLES AND METHOD FOR PREPARING THE SAME

CROSS-REFERENCE TO RELATED APPLICATION

This application claims priority to and the benefit of Korean Patent Application No. 2016-0049854, filed on Apr. 25, 2016, the disclosure of which is incorporated herein by reference in its entirety.

BACKGROUND

1. Field of the Invention

The present invention relates to a gene carrier using cell-derived nanovesicles and a method for preparing the same.

2. Discussion of Related Art

Gene therapy is a treatment of a disease by delivering a therapeutic gene to a desired organ in the body to express a new protein in a cell, and recently, its valid therapeutic effects on various diseases such as viral diseases, cancer and the like have been widely reported. As the initial gene therapeutic agent has been commercially available in Europe, active studies on this are also progressing in Korea. Actually, some gene therapeutic agents show excellent therapeutic effects in clinical trials, and therefore expectations are high for the development of gene therapeutic agents not only in Korea but also around the world. However, even with such attention, gene therapeutic agents have not shown high efficacy in early clinical trials, and thus it is extremely rare that they are actually commercialized. Main causes for this are safety of a gene therapeutic agent and low gene delivery efficiency to a target cell. Accordingly, for effective gene therapy, it is necessary to develop a gene carrier capable of achieving high expression efficiency by safely delivering a therapeutic gene to a desired target cell.

Today, while viral gene carriers with high delivery efficiency have been most widely used, viral vectors such as a retrovirus, an adenovirus, and an adeno-associated virus have many limitations in being applied to the human body because of a complicated production process, safety problems such as immunogenicity, infection potential, inflammation induction and non-specific DNA insertion, and a limited size of acceptable nucleic acids. For this reason, today, non-viral gene carriers have attracted attention as an alternative to viral gene carriers (Korean Unexamined Patent Application No. 2014-0118458). Non-viral gene carriers can be repeatedly administered due to minimal immune responses, specifically delivered to specific cells, have excellent safety and storage stability, and facilitate mass production. Examples of the non-viral gene carriers include cationic liposome-like carriers such as N-[1-(2,3-dioleyloxy)propyl]-N,N,N-trimethylammonium chloride (DOTMA), alkyl ammonium, cationic cholesterol derivatives, gramicidin, etc. However, these carriers also have disadvantages in that they have low blood stability, low gene delivery efficiency and low competitive prices.

In light of this, although there is an urgent demand for development of a gene carrier which has high delivery efficiency as well as the advantages of a conventional viral gene carrier, there is much to be desired.

SUMMARY OF THE INVENTION

To solve the problems described above, the inventors had confirmed that a gene can be efficiently introduced into a target cell by a gene carrier using nanovesicles which are artificially outbudded from a plasma membrane, and based on this, completed the present invention.

Therefore, the present invention is directed to providing a gene carrier based on cell-derived nanovesicles and a method for preparing the same.

However, technical problems to be achieved by the present invention are not limited to the above-described problems, and other problems which are not described will be clearly understood by those of ordinary skill in the art from the following description.

In one aspect, the present invention provides a method for preparing a gene carrier, the method including: (a) preparing nanovesicles through extrusion of a suspension containing vesicles outbudded from cells; and (b) inserting a nucleotide into the prepared nanovesicle.

In another aspect, the present invention provides a method for preparing a gene carrier, the method including: (a) preparing microvesicles by centrifuging a suspension containing vesicles outbudded from cells; (b) treating the microvesicles with a surfactant and a nucleotide to insert the nucleotide into the microvesicles; and (c) preparing nanovesicles by extruding a suspension containing the nucleotide-inserted microvesicles.

In still another aspect, the present invention provides a gene carrier based on cell-derived nanovesicles, which is prepared by the above-described method.

In yet another aspect, the present invention provides a use of the gene carrier to be applied as a component for a gene therapeutic agent or a cell therapeutic agent.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which:

FIG. 3 shows the results of (a) observing nanovesicles of the present invention by transmission electron microscopy, and (b) size distribution through dynamic light scattering;

FIG. 4 shows (a) nanovesicle production per single cell and (b) production per single cells per unit time according to a preparation method of the present invention;

FIG. 5 shows a result for confirming (a) intracellular uptake by fluorescence, and (b) an intracellular uptake quantified by a RiboGreen assay, after siRNAs labeled with Cy5 are delivered to cells using the nanovesicles of the present invention;

FIG. 14 shows a degree of calcium precipitation confirmed by Alizarin S staining, after GNAS siRNAs are delivered to hADSCs using the gene carrier of the present invention;

FIG. 16 shows a result of quantifying expressions of (a) Nestin, (b) GFAP, (c) olig2, (d) Tuj1, and (e) MAP2, after REST siRNAs are delivered to hfNSCs using the gene carrier of the present invention;

FIG. 24 shows (a) a real-time imaging analysis result, (b) a fluorescence intensity measurement result, (c) a fluorescence imaging analysis result per organ, and (d) a fluorescence intensity measurement result per organ after APOB siRNAs are delivered to a mouse animal model using the gene carrier of the present invention;

FIG. 26 shows results of measuring (a) AST concentration and (b) ALT concentration in blood after APOB siRNAs are delivered to a mouse animal model using the gene carrier of the present invention.

DETAILED DESCRIPTION OF EXEMPLARY EMBODIMENTS

Figure 1:
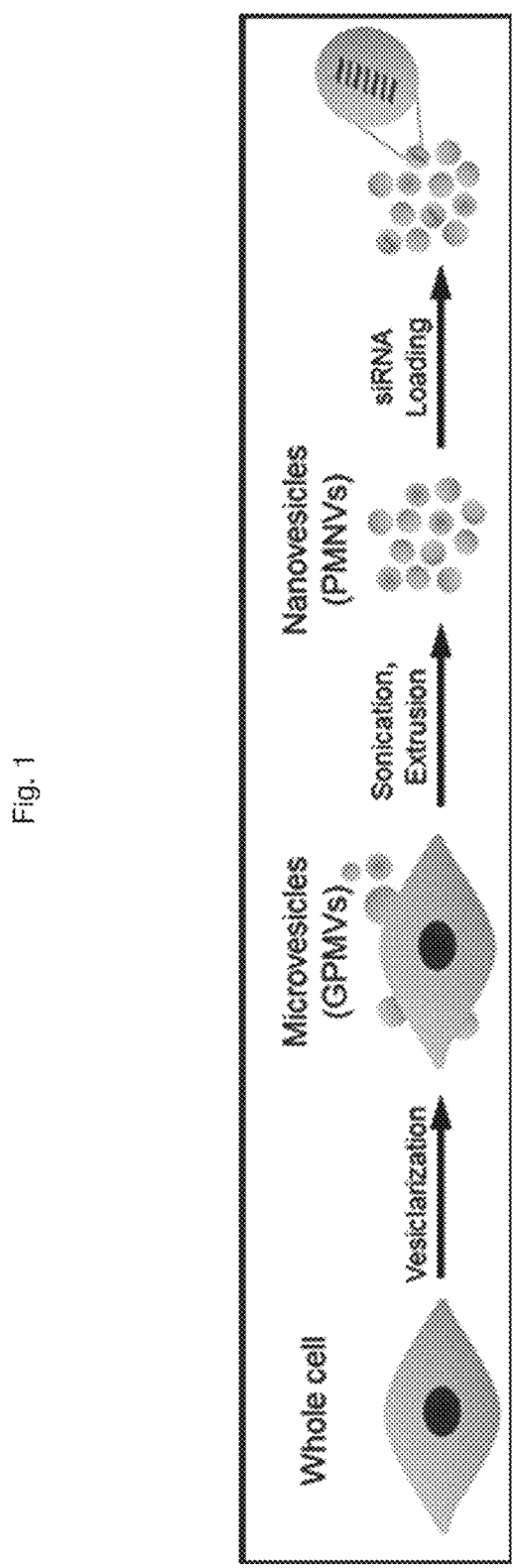
FIG. 1 is a schematic diagram illustrating a process of preparing a gene carrier for RNA delivery.
Figure 2:
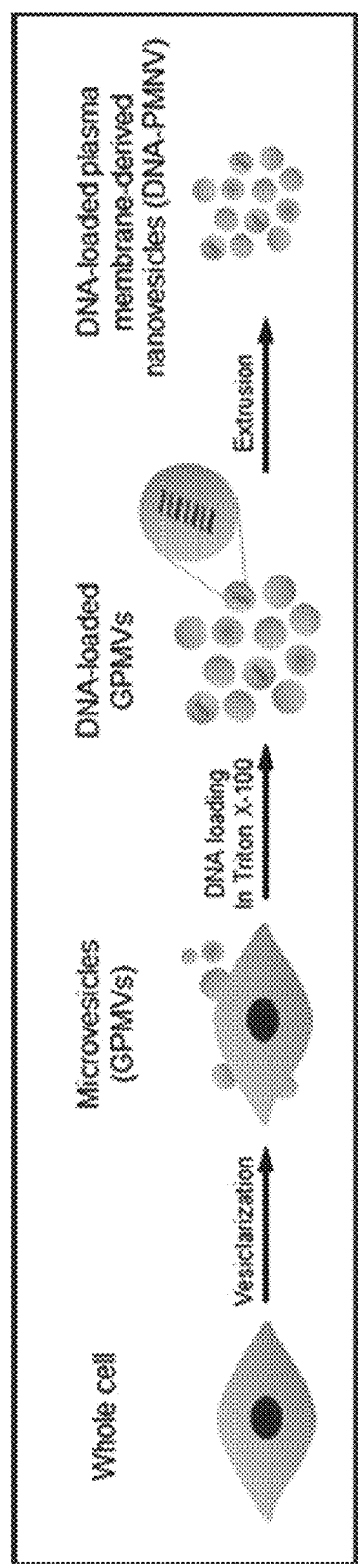
FIG. 2 is a schematic diagram illustrating a process of preparing a gene carrier for DNA delivery.

Hereinafter, the present invention will be described in detail.

The present invention provides a method for preparing a gene carrier, which includes: (a) preparing nanovesicles by extruding a suspension containing vesicles outbudded from cells; and (b) inserting nucleotides into the prepared nanovesicles, in which the nucleotides are selected from the group consisting of mRNA, tRNA, rRNA, siRNA, and miRNA.

In addition, the present invention provides another method for preparing a gene carrier, which includes: (a) preparing microvesicles by centrifuging a suspension containing vesicles outbudded from cells; (b) treating the microvesicles with a surfactant and nucleotides to insert the nucleotides into the microvesicles; and (c) preparing nanovesicles by extruding a suspension containing the nucleotide-inserted microvesicles, in which the nucleotides are selected from the group consisting of gDNA, pDNA, and cDNA.

The vesicles of the present invention may be prepared to have a nano-scale diameter for effective gene delivery, which is preferably, but not limited to, 100 to 200 nm. When the diameter is below the above range, it is difficult to perform the insertion of the nucleotides, and when the diameter is very large, gene introduction efficiency might be reduced. In addition, the nanovesicles may be prepared using any one method selected from the group consisting of extrusion, sonication, cell lysis, homogenization, freezing-thawing, electroporation, mechanical degradation, and chemical treatment, and preferably by culturing vesicles in a PFA and DTT-added buffer solution to outbud them from cells, and extruding a suspension containing the vesicles. Here, to enhance a production yield of the vesicles, a PFA concentration may be 25 mM or more, preferably 25 to 50 mM, and most preferably 25 mM, and a DTT concentration may be 1 mM or more, preferably 1 to 5 mM, and most preferably 1 mM, but the present invention is not limited thereto.

Meanwhile, while exosomes released from cells for the purpose of intercellular signaling have been widely used as conventional cell-derived gene carriers, the exosomes contain inherent genetic substances of cells such as RNAs, proteins, etc., and thus there is difficulty in regulating their internal compositions. However, in one exemplary embodiment, for outbudding cell-derived vesicles in a HEPES buffer, the nanovesicles or gene carrier prepared by the above method may be prepared to contain the HEPES buffer as a main component. That is, since the internal composition of the nanovesicles may be easily regulated according to the type of a buffer treated to cells, an influence of the genetic substances of the cell itself may be minimized. Here, the buffer solution may be a HEPES buffer, a PBS buffer, or a HBSS buffer, and has no limitation in use, as long as it can change the internal composition of the nanovesicles.

In addition, before Step (a), the delivery efficiency of the gene carrier with respect to specific cells may be enhanced by transforming, that is, overexpressing a targeting ligand to the cells.

The term "transformation" used herein refers to a molecular biological technique for changing the genetic characteristic of a cell by penetrating a DNA strand fragment or plasmid, which contains a different type of a foreign gene from the original one of the cell, into the cell to be bound with DNA originally present in the cell. In the present invention, the transformation refers to the overexpression of a targeting ligand in a plasma membrane to enhance the delivery efficiency to target cells. As an exemplary embodiment, the delivery efficiency to hiPSCs and human adipose stem cells (hADSCs) may be enhanced using E-cadherin as a targeting ligand, and any ligand capable of binding to specific cells may be used without limitation.

However, when the nucleotide to be enclosed by the gene carrier is DNA such as gDNA, pDNA or cDNA, which has a relatively larger size than RNA, first, the microvesicles are treated with a surfactant and the nucleotide to insert the nucleotide, and then extruded, thereby preparing a nanoscale gene carrier. The surfactant is a substance treated to reduce the surface tension of the microvesicles to allow DNA to be inserted into the vesicles, and is preferably Triton X-100, but the present invention is not limited thereto.

In one experimental example of the present invention, since the nanovesicles prepared by the method of the present invention have physical properties similar to the exosomes, they may be used as a gene carrier, and further it was identified that they are easily used for mass production and gene delivery, compared to the exosomes, and uniformly maintained intracellular uptake of a gene even with a difference in buffer solution (refer to Experimental Examples 1 and 2). In addition, in another exemplary embodiment of the present invention, in vitro and in vivo examinations were carried out to confirm that expression of a differentiation-involved gene in various cells, particularly, in stem cells, may be effectively regulated using the nanovesicle-based gene carrier (refer to Experimental Examples 3 and 5), and the delivery efficiency of the gene carrier may be enhanced by introducing a targeting ligand. Here, it was experimentally determined that even when inserting DNA as well as RNA, the gene carrier may exhibit excellent delivery efficiency (refer to Experimental Examples 4 and 6).

Therefore, the present invention provides a gene carrier which includes cell-derived nanovesicles prepared by the above preparation method and a nucleotide enclosed by the nanovesicles.

The term "nanovesicles" or "microvesicles" used herein refers to vesicles which are prepared by being artificially outbudded from cells, more specifically, a plasma membrane, and serve to deliver a nucleotide into target cells. The nanovesicles are distinguished from naturally released "shedding microvesicles," and the vesicles of the present invention have the inside which is separated from the outside by a lipid bilayer composed of plasmid membrane components.

In one aspect, the present invention provides a gene carrier for promoting stem cell differentiation prepared by the above-described preparation method, which includes cell-derived nanovesicles and a nucleotide enclosed by the nanovesicles.

The term "stem cells" used herein refers to cells having a self-replication ability and an ability to differentiate into new cells, and may be classified into totipotent stem cells, pluripotent stem cells, and multipotent stem cells according to differentiation ability, and also classified into adult stem cells, embryonic stem cells and dedifferentiated stem cells according to tissue from which the stem cells originate. In the present invention, the stem cells are cells in which differentiation is promoted by the gene carrier provided in the present invention, and preferably stem cells derived from the bone marrow, adipose tissue, teeth, dental tissue, blood, cord blood, liver, skin, gastrointestinal tract, placenta, womb, or a fetus, but the present invention is not limited thereto.

In addition, in another aspect, the present invention provides a use of the gene carrier which can be applied as a component for a gene therapeutic agent or a cell therapeutic agent.

Hereinafter, exemplary examples will be provided to help in understanding of the present invention. However, the following examples are merely provided to facilitate understanding of the present invention, and the scope of the present invention is not limited to the following examples.

PREPARATION EXAMPLES

Preparation Example 1. Preparation of Gene Carrier Based on Cell-Derived Nanovesicles 1-1. Preparation of Gene Carrier for RNA Delivery In a HEPES buffer (10 mM HEPES, 150 mM NaCl, 2 mM $CaCl_2$, pH 7.4) containing 25 mM parformaldehyde (PFA) and 2 mM dithiothreitol (DTT), a HEK-293 cell line was incubated at 37° C. for 3 to 4 hours to artificially outbud vesicles from the cells, and the culture dish was shaken every 30 minutes to obtain a higher yield of vesicles. Subsequently, the resulting suspension containing the vesicles was sequentially subjected to centrifugation, sonication and extrusion, thereby preparing cell-derived nanovesicles with a uniform size. Afterward, a nucleic acid molecule composed of RNA was introduced into the nanovesicles using electroporation, resulting in the preparation of a gene carrier for RNA delivery.

1-2. Production of Gene Carrier for DNA Delivery

According to the same method as described in Preparation Example 1-1, a HEK-293 cell line was incubated to artificially outbud vesicles and centrifuged (20,000 g, 60 min), thereby obtaining cell-derived microvesicles. Subsequently, a nucleic acid molecule composed of DNA was introduced into the microvesicles by treatment with 10 mM Triton X-100, and then the microvesicles were incubated with a bio-bead resin at 4° C. to remove any remaining Triton X-100. Afterward, the DNA-inserted cell-derived microvesicles were extruded into nano-scale vesicles, thereby preparing a gene carrier for DNA delivery.

In the following experimental examples, the cell-derived nanovesicles prepared by being outbudded from cells according to Preparation Examples 1-1 and 1-2 were named nanovesicles.

EXPERIMENTAL EXAMPLES

Experimental Example 1. Analysis of Physical Properties of Nanovesicles

Exosomes are cell-derived natural substances, which have been known, according to a recent report, to be used as a gene carrier. Therefore, in this experimental example, physical properties of the nanovesicles prepared in Preparation Example 1-1 (plasma membrane-derived nanovesicles; PMNVs) were compared with those of the exosomes.

Specifically, a nanovesicle structure was observed using a transmission electron microscope (TEM), a zeta potential was measured by dynamic light scattering (DLS) and nanoparticle tracking analysis (NTA), and production per single cell and production per single cell per unit time were measured to compare productivities. In addition, fluorescence intensities were measured when Cy5-labeled siRNAs were delivered by simple mixing and by insertion, so as to verify that a gene carrier using nanovesicles or exosomes can be internalized in cells, and a quantity of siRNA inserted into the nanovesicles or exosomes through electroporation was measured by a RiboGreen assay to compare intracellular uptake thereof.

Consequently, as shown in FIG. 3 and Table 1 below, the outer surface of the nanovesicles (PMNVs) of the present invention was enclosed by a membrane, which is similar to the exosome structure (refer to FIG. 3A), the nanovesicle diameter was usually observed in a range from 100 to 200 nm (refer to FIG. 3B), and the average diameter and the zeta potential were 139.21±1.91 nm and −11.59±1.41 $\zeta$, respectively, which are similar to those of the exosomes. Therefore, it can be confirmed that the nanovesicles are suitable as a gene carrier.

TABLE 1

|  | Size (nm) | Zeta-potential ($\zeta$) |
|---|---|---|
| Exosome | 136.85 ± 2.45 | −14.27 ± 3.98 |
| PMNV | 139.21 ± 1.91 | −11.59 ± 1.41 |

In addition, as shown in FIGS. 4 and 5, the nanovesicles (PMNVs) of the present invention were considerably increased in production per single cell (FIG. 4A) or production per single cells per unit time (FIG. 4B), compared to those of the exosomes, indicating that it is preferable for mass production (refer to FIG. 4). Not only that, as a result of confirming intracellular uptake, when a nucleic acid molecule was delivered by simple mixing, fluorescence was not detected in cells, but when siRNAs were transferred by being inserted into the nanovesicles or exosomes, strong fluorescence was observed (refer to FIG. 5A). While the siRNA uptake was 25.3% in the case of the gene carrier using the exosomes, and the siRNA uptake was 31.6% in the case of the gene carrier using the nanovesicles, which shows that the intracellular uptake was significantly increased (refer to FIG. 5B). From the this result, it can be seen that, like the previously-reported exosomes, the nanovesicles of the present invention can be used as a gene carrier, and due to such a nanovesicle-based gene carrier, the intracellular uptake of the gene is further increased.

Experimental Example 2. Comparison of Nanovesicle Yields and Gene Delivery Efficiency According to Treatment Condition 2-1. Comparison of Nanovesicle Yields According to PFA and DTT Treatment Conditions In the preparation of the gene carrier of Preparation Example 1, a large quantity of vesicles could be artificially outbudded from cells by culturing the cells in a PFA and DTT-added HEPES buffer. In this experimental example, to deduce the optimal conditions for further enhancing the production yield of nanovesicles, various concentrations of PFA (5 mM, 25 mM, and 50 mM) or DTT (0.25 mM, 1 mM, and 2 mM) were added to a buffer solution, and the nanovesicles were prepared by the same method as described in Preparation Example 1-1 under conditions in which the DTT concentration was constantly maintained at 1 mM while the PFA concentration varied, and the PFA concentration was constantly maintained at 25 mM while the DTT concentration varied. Afterward, the nanovesicle yields per treatment concentration were quantitatively compared.

Figure 6:
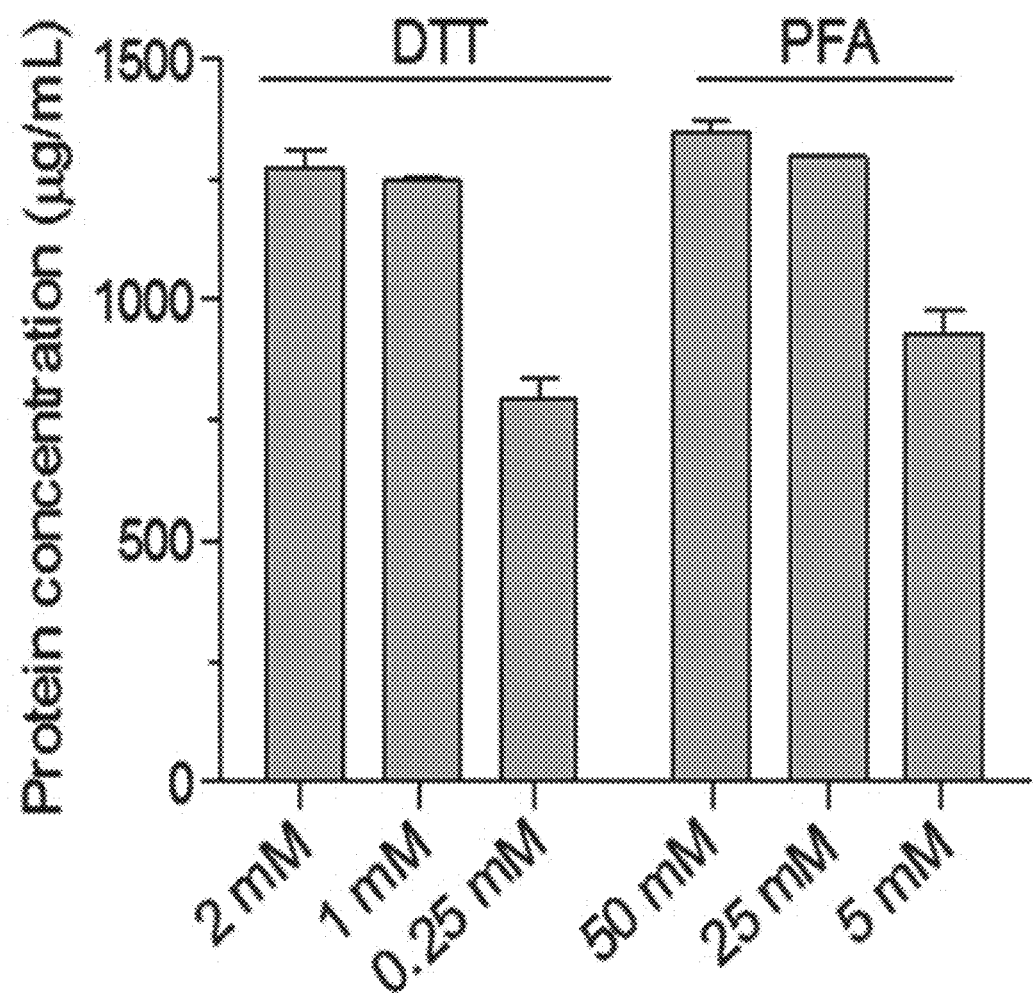
FIG. 6 shows a result of comparing yields of nanoparticles according to a difference in paraformaldehyde (PFA) and dithiothreitol (DTT) treatment concentrations in the preparation method of the present invention.

Consequently, as shown in FIG. 6, it can be confirmed that, from when the concentration of PFA added to the buffer solution was 25 mM and the DDT concentration was 1 mM or more, the nanovesicle yield was considerably increased.

2-2. Comparison of Gene Delivery Efficiency According to Buffer

While exosomes that have been currently used as a gene carrier may reduce delivery efficiency since containing genetic substances such as RNAs, proteins, etc. of a cell itself, the gene carrier of Preparation Example 1 employs vesicles containing the buffer solution used for culturing as a major component, and therefore the internal composition of the vesicles may be regulated as needed. In this experimental example, to verify that original gene delivery efficiency can be maintained even with a change in buffer solution, EGFP siRNA (siEGFP)-introduced gene carriers were prepared by the same method as described in Preparation Example 1-1 using various buffer solutions (HEPES, PBS and HBSS), and then each gene carrier was delivered into cells. Subsequently, fluorescence intensities of the gene carriers were measured to compare gene delivery efficiency. Meanwhile, as controls, a group to which siRNAs are not delivered (NT) and a scrambled siRNA (siSCR)-inserted group were used.

Figure 7:
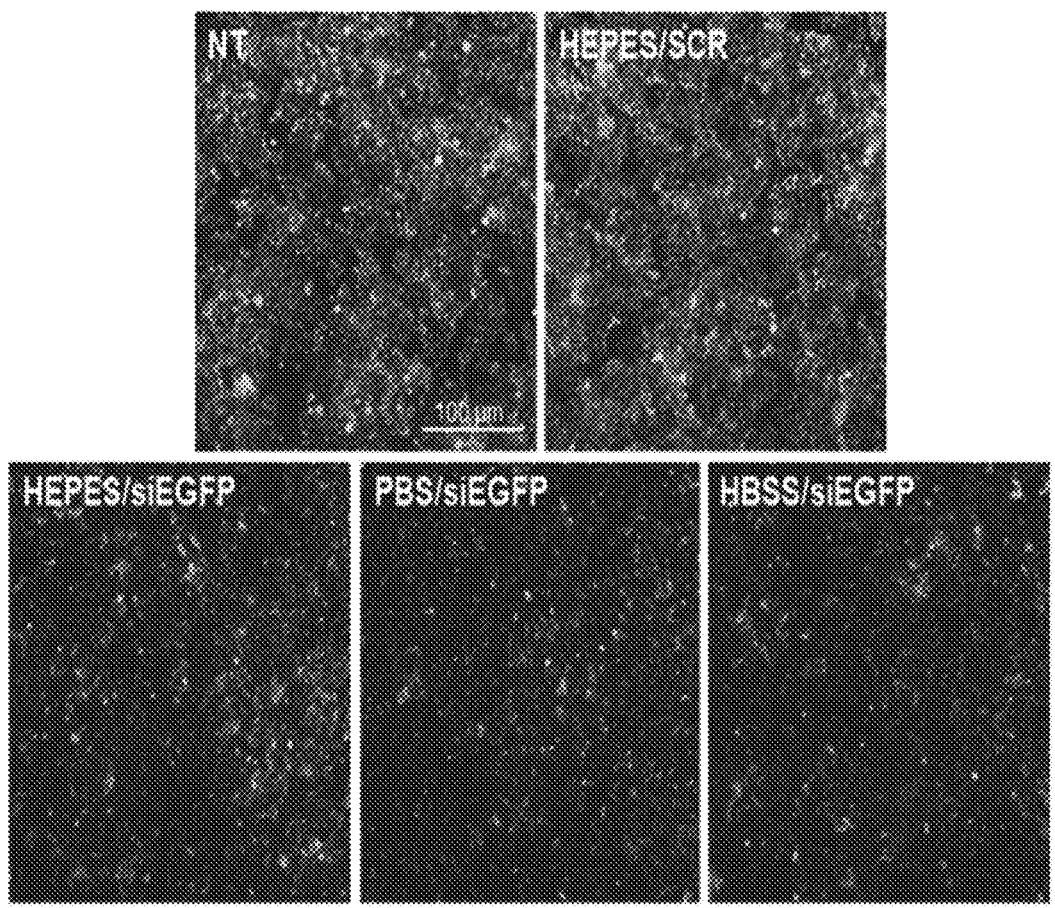
FIG. 7 shows a result of comparing gene delivery efficiency according to a difference in buffer solutions (HEPES, PBS and HBSS) in the preparation method of the present invention.

Consequently, as shown in FIG. 7, it can be confirmed that, even when the compositions of the buffer solutions (HEPES, PBS, HBSS, pH7.4) varied, there were no significant differences in fluorescence intensity, indicating that the gene delivery efficiency is uniformly maintained.

Experimental Example 3. Intracellular siRNA Delivery by Gene Carrier of the Present Invention 3-1. Analysis of Intracellular siRNA Delivery Efficiency In this experimental example, a gene carrier was prepared by inserting siEGFPs into the nanovesicles of Preparation Example 1-1 and then delivered to a HeLa cell line, the efficiency of reducing EGFP expression achieved thereby was quantified using fluorescence microscopy and flow cytometry (FACS), and cytotoxicity was evaluated by an MTT test. In addition, siRNAs of glyceraldehyde-3-phosphate dehydrogenase (GAPDH), which is a housekeeping gene, were inserted into the nanovesicles of the present invention, thereby preparing a gene carrier, and then delivered to human adipose-derived stem cells (hADSCs), and human fetal neural stem cells (hfNSCs). Afterward, decreases in expression and cytotoxicity for each were evaluated. The GAPDH expression was measured as a relative expression ratio with respect to an ACTB gene. Meanwhile, as a control, a group to which siRNAs are not delivered (NT), and as comparative groups, lipofectamine 2000 (LF 2000) and exosomes (Exo), which have been currently commercialized, were used. Specifically, in the case of a gene carrier using the LF 2000, a gene carrier in which siRNA and LF 2000 were mixed was prepared by mixing 1 μg LF 2000 per 20 pmol siRNA, and incubating the mixture for 10 minutes. In addition, in the case of a carrier using exosomes (Exo), first, cells were cultured in exosome-free media for 36 to 48 hours, and the culture solution obtained therefrom was subjected to ultracentrifugation twice, and following washing, the exosomes were subjected to electroporation with siRNAs at a 1:1 wt/wt ratio, thereby preparing a gene carrier in which siRNAs were encapsulated in the exosomes.

Figure 8A:
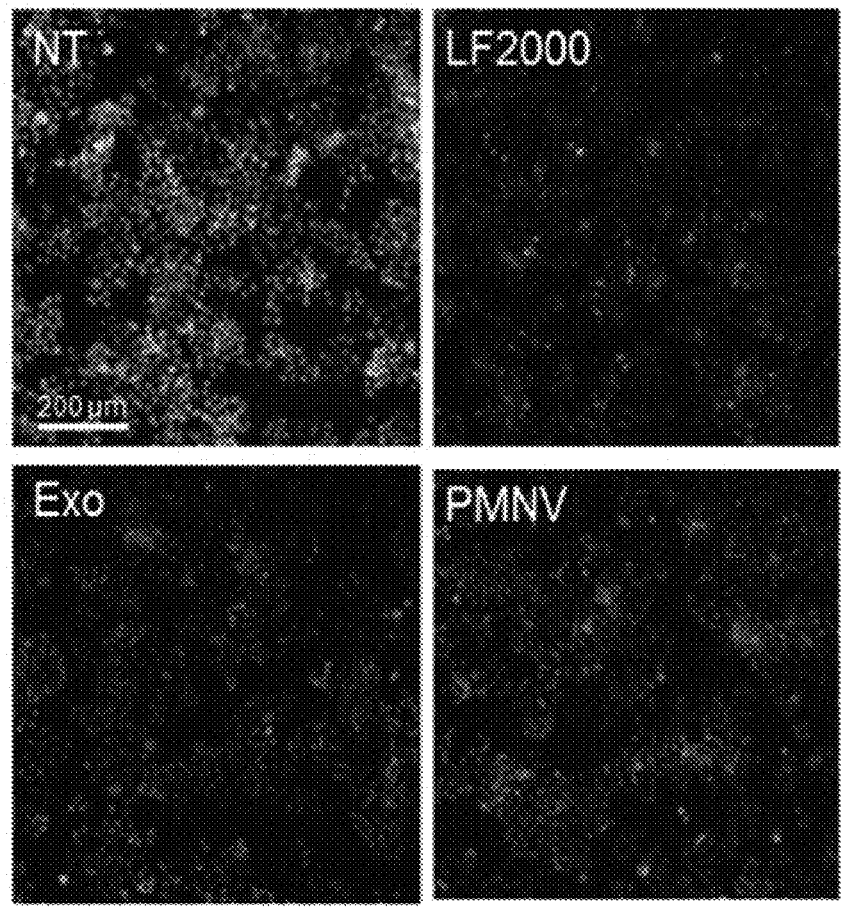
FIG. 8 shows the results of confirming enhanced green fluorescent protein (EGFP) expression with (a) a fluorescence microscope and (b) flow cytometry, after EGFP siRNA is delivered to a HeLa cell line using the gene carrier of the present invention.
Figure 8B:
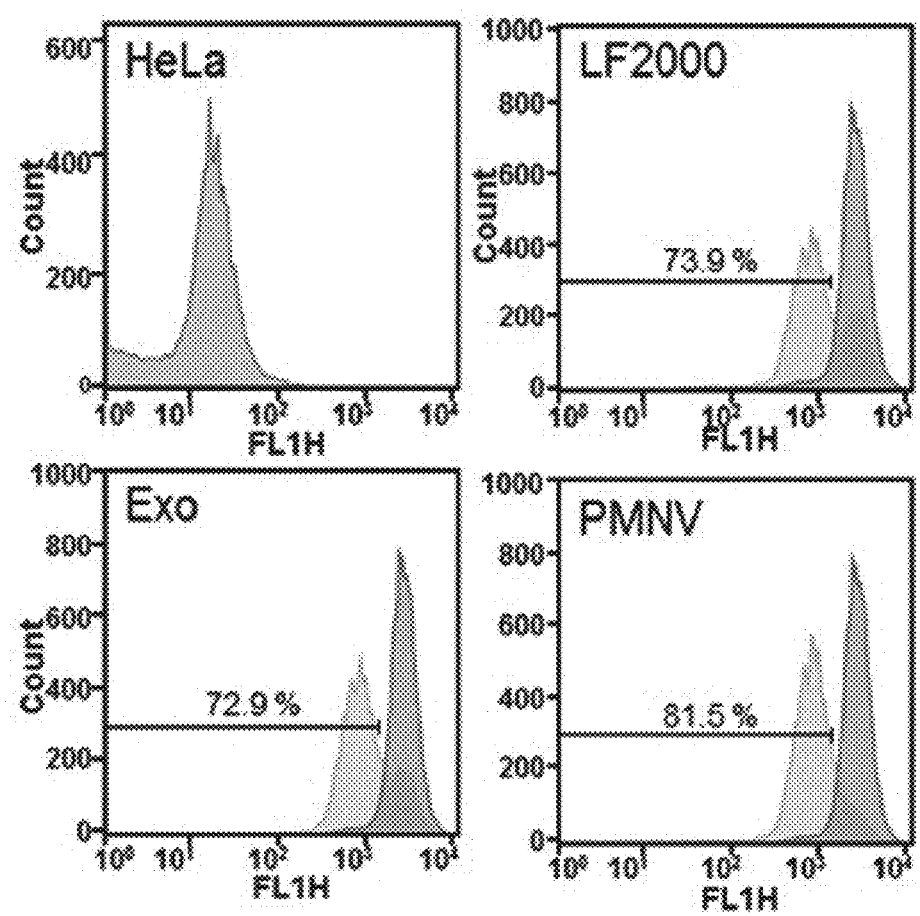
Figure 9A:
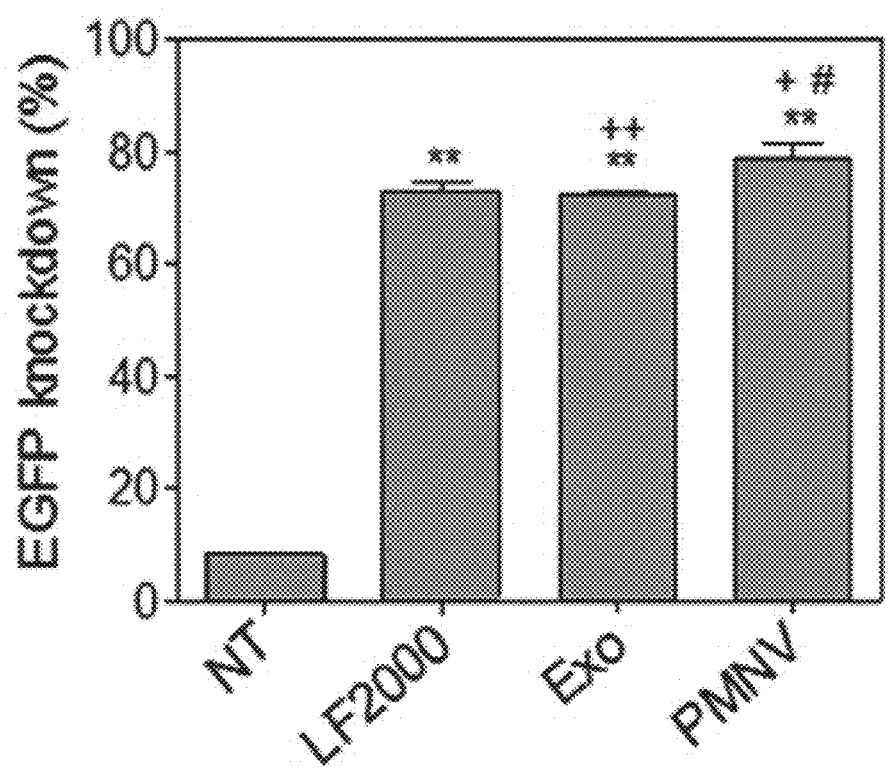
FIG. 9 shows the results of (a) quantifying EGFP expression and (b) evaluating cytotoxicity, after EGFP siRNA is delivered to a HeLa cell line using the gene carrier of the present invention.
Figure 9B:
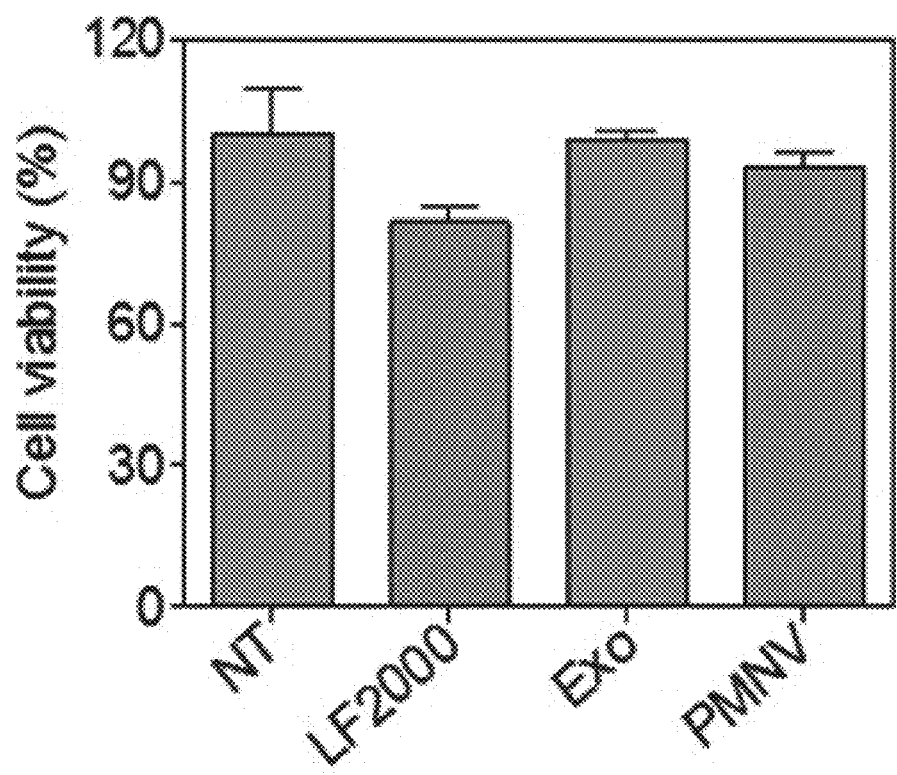
Figure 10B:
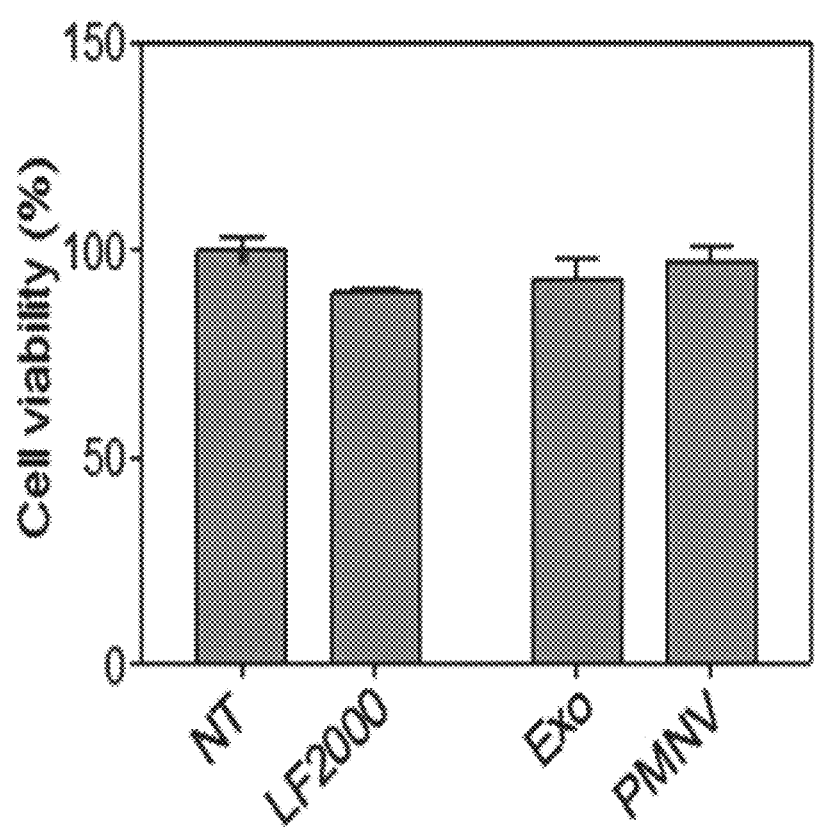
FIG. 10 shows the results of (a) quantifying GAPDH expression and (b) evaluating cytotoxicity, after GAPDH siRNAs are delivered to human adipose-derived stem cells (hADSCs) using the gene carrier of the present invention.
Figure 11B:
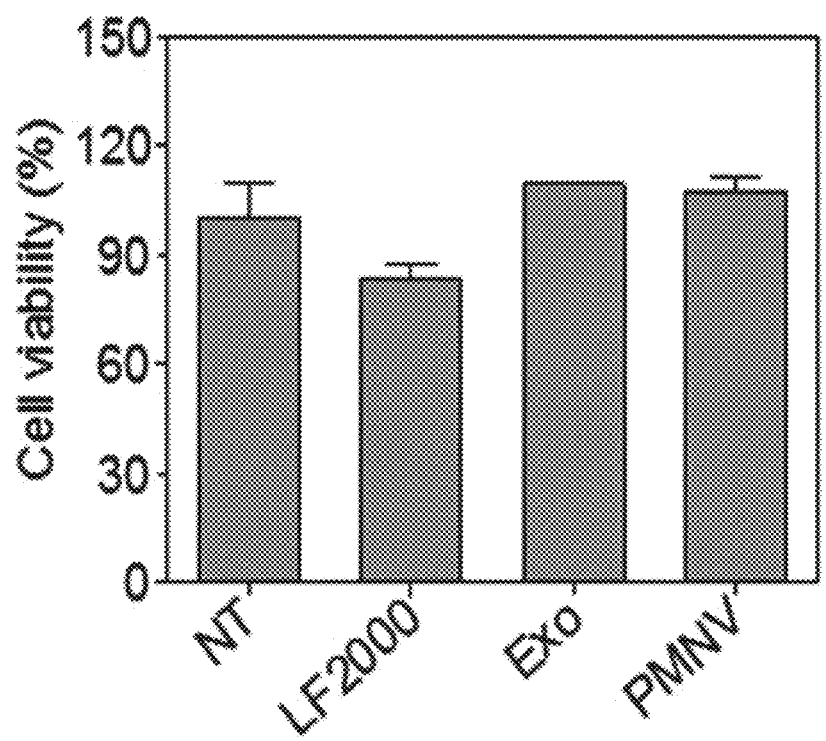
FIG. 11 shows the results of (a) quantifying GAPDH expression and (b) evaluating cytotoxicity, after GAPDH siRNAs are delivered to human fetal neural stem cells (hfNSCs) using the gene carrier of the present invention.

Consequently, as shown in FIGS. 8 and 9, in a HeLa cell line, expression reduction ratios of the groups using the LF 2000 and the exosomes were merely 73.9% and 72.9%, respectively, whereas, when the gene carrier (PMNV) of the present invention was used, the reduction ratio was significantly increased to 81.5%, and low cytotoxicity was exhibited as in the comparative groups. Like this result, as shown in FIGS. 10 and 11, in hADSCs and hfNSCs, GAPDH expression was further reduced and low cytotoxicity was exhibited due to the gene carrier of the present invention. From this result, it can be seen that a genetic substance can be delivered with high efficiency to various cells through the delivery technique of the present invention without side effects such as cytotoxicity.

3-2. Enhancement in Bone Cell Differentiation Efficiency According to GNAS siRNA Delivery In this experimental example, after siRNAs of GNAS, which is a bone differentiation inhibitory protein, were delivered to hADSCs using the gene carrier of the present invention, a decrease in GNAS mRNA expression caused thereby was measured as a relative expression ratio with respect to a GAPDH gene, increases in expression of COL1A2 and OPN, which are bone cell markers, were verified by qRT-PCR and immunostaining analysis, and calcium precipitation caused by the decrease in GNAS expression was evaluated using Alizarin S staining. Meanwhile, a group to which siRNAs are not delivered (NT) was used as a control, and LF 2000, which is currently commercialized, and exosomes were used as comparative groups.

Figure 12:
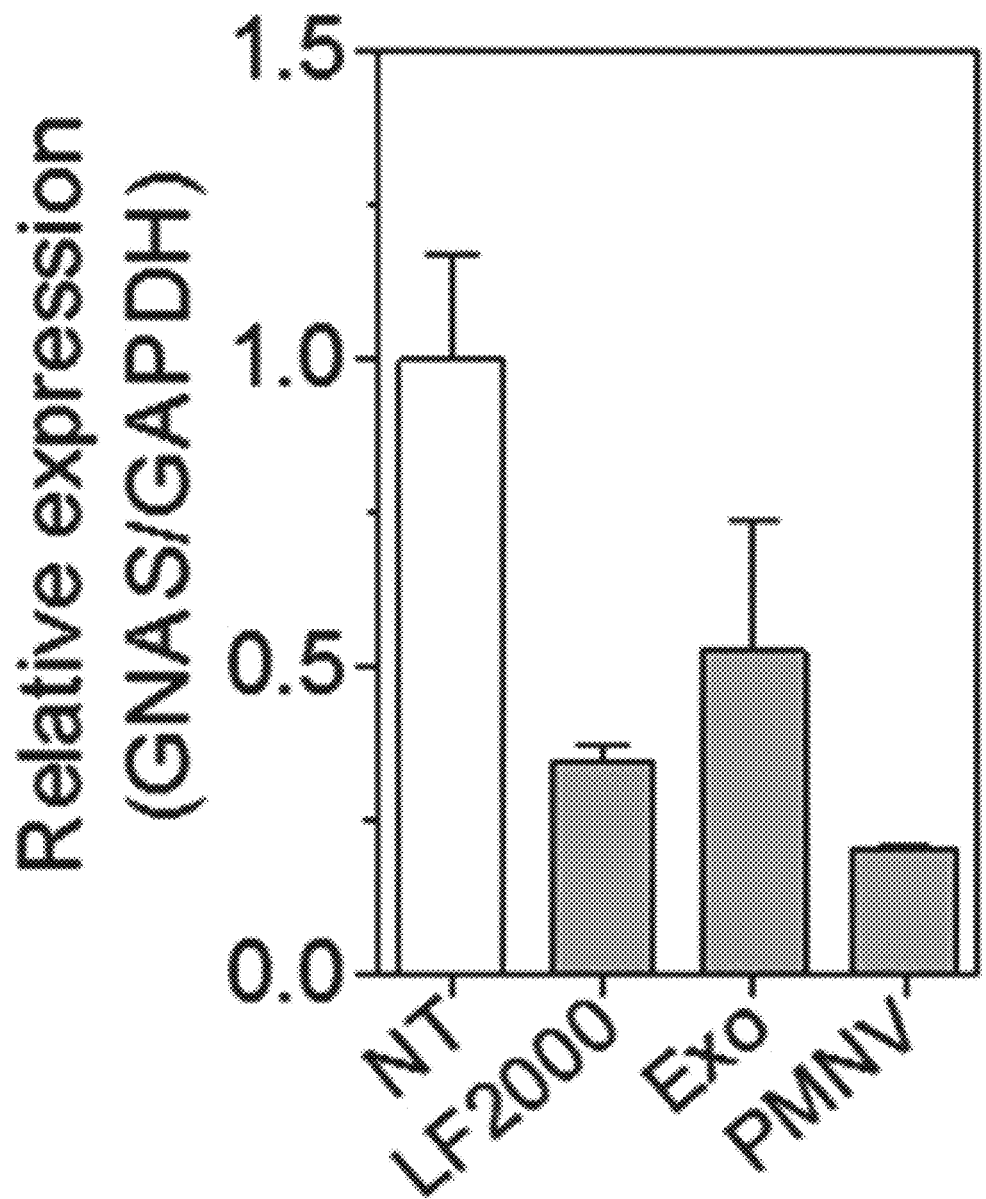
FIG. 12 shows a result of quantifying GNAS expression after GNAS siRNAs are delivered to hADSCs using the gene carrier of the present invention.
Figure 13A:
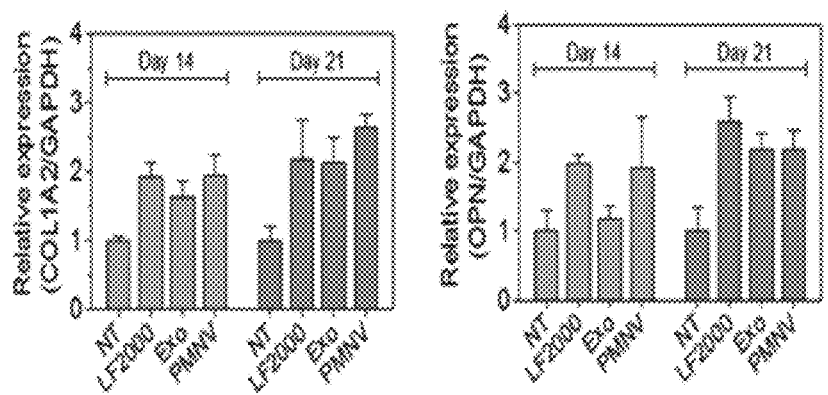
FIG. 13 shows a result of (a) quantifying COL1A2 and OPN expression over time and (b) observation by fluorescence microscopy, after GNAS siRNAs are delivered to hADSCs using the gene carrier of the present invention.
Figure 13B:
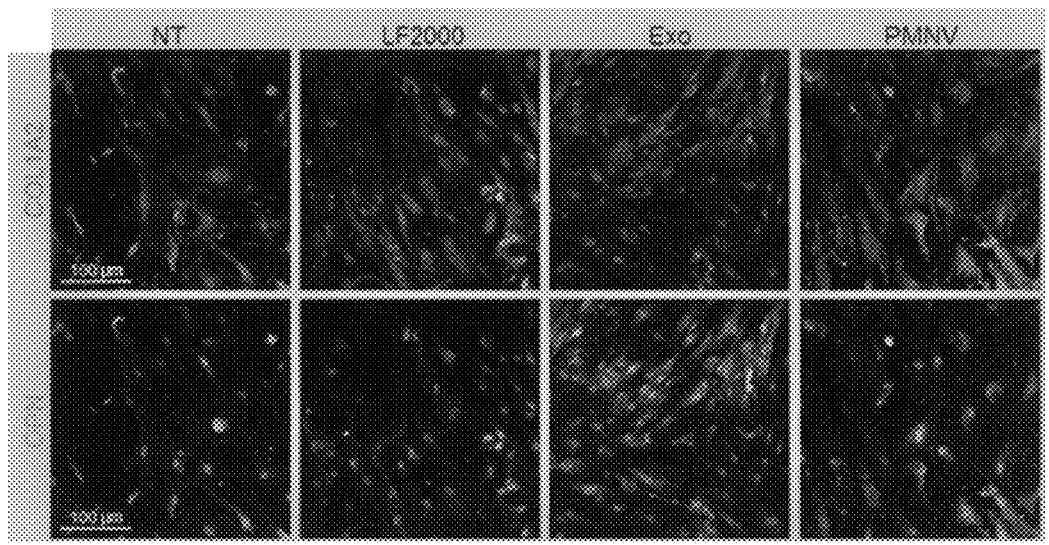

Consequently, as shown in FIGS. 12 and 13, it can be confirmed that, by using the gene carrier (PMNV) of the present invention, the GNAS expression was further reduced compared to the comparative groups (refer to FIG. 12), and the expression of COL1A2 and OPN, which are bone cell markers, was considerably increased, compared to the control (refer to FIG. 13). In addition, as a result of evaluating calcium precipitation in hADSCs, as shown in FIG. 14, it can be confirmed that the calcium precipitation was detected at the highest level when the gene carrier of the present invention was used. Therefore, it can be seen that the technique of the present invention can promote differentiation into bone cells from hADSCs.

3-3. Enhancement in Neuronal Differentiation Efficiency According to REST siRNA Delivery In this experimental example, after siRNAs of RE1-silencing transcription factor (REST), which is a neuronal differentiation inhibitory protein, were delivered to hfNSCs using the gene carrier of the present invention, 2 days after the REST siRNA delivery, a decrease in REST mRNA expression was measured as a relative expression ratio with respect to a GAPDH gene. Likewise, 5 to 9 days after the REST siRNA delivery, the expression of Nestin and GFAP, which are early neuronal markers, and olig2, Tuj1 and MAP2, which are late neuronal markers, was measured, and a change in neurite length according to the decrease in REST expression was observed using immunostaining. Meanwhile, a group to which siRNAs are not delivered (NT) was used as a control, and LF 2000 which is being current commercialized was used as a comparative group.

Figure 15:
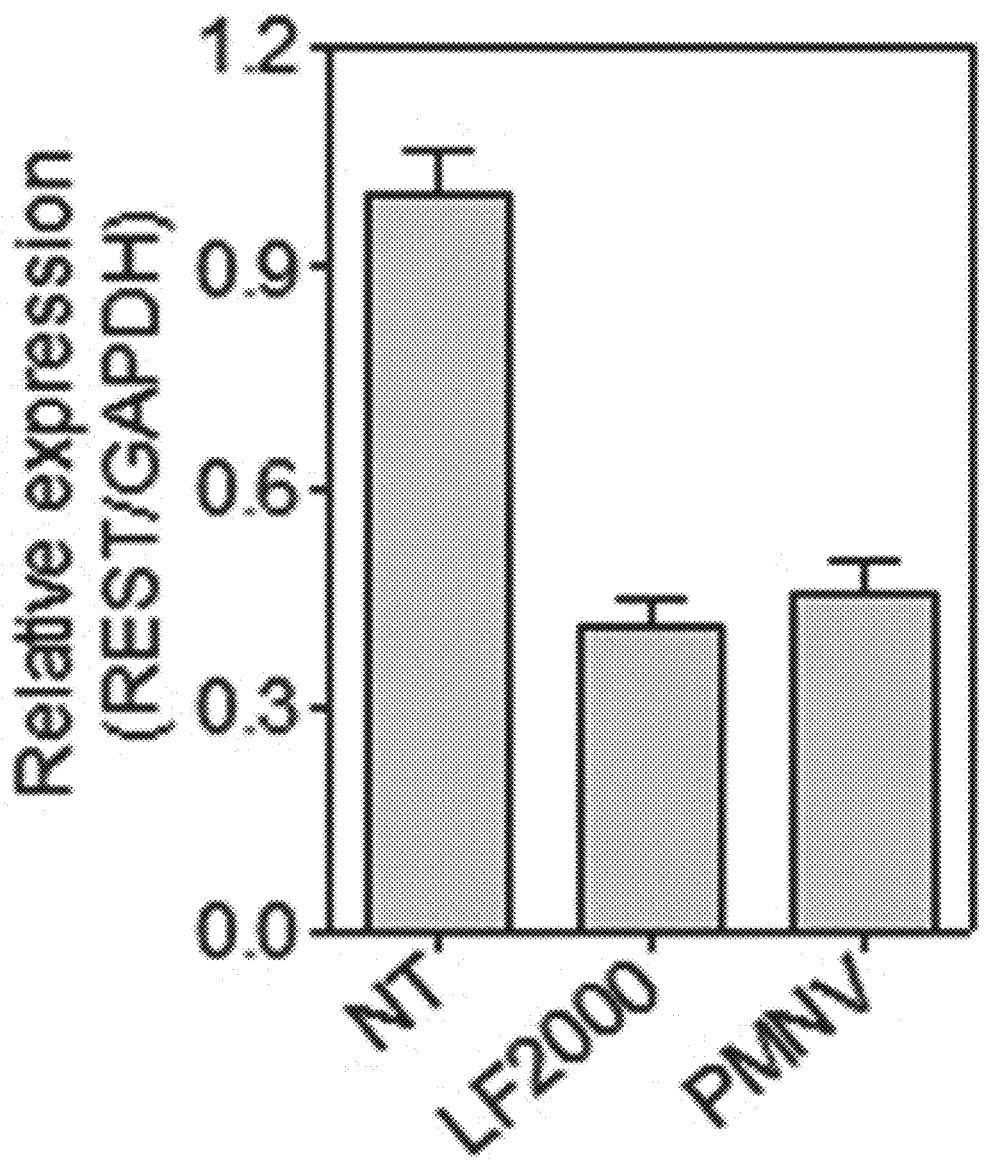
FIG. 15 shows a result of quantifying REST expression after REST siRNAs are delivered to human fetal neural stem cells (hfNSCs) using the gene carrier of the present invention.
Figure 17A:
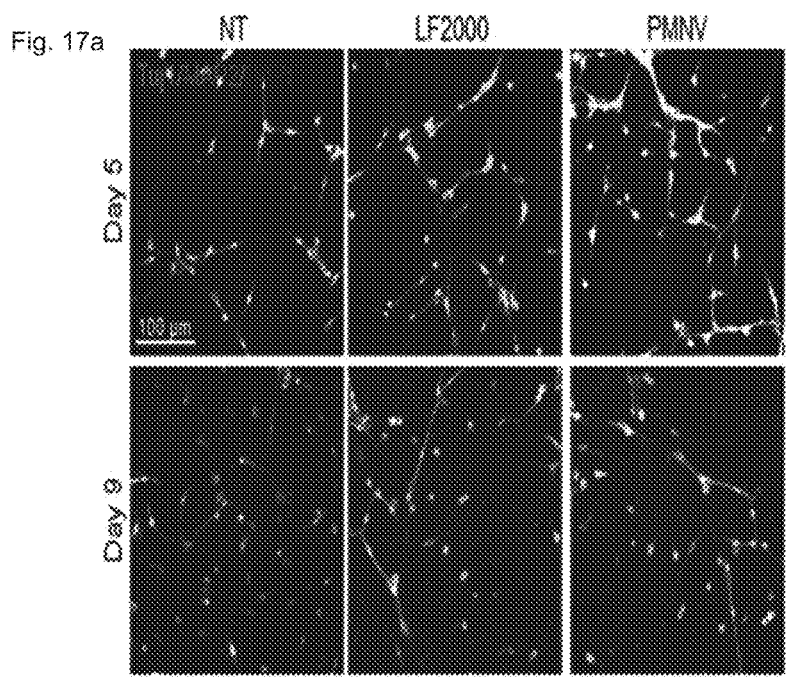
FIG. 17 shows the results of (a) observing a neurite length by fluorescence microscopy and (b) a quantification result thereof, after REST siRNAs are delivered to hfNSCs using the gene carrier of the present invention.
Figure 17B:
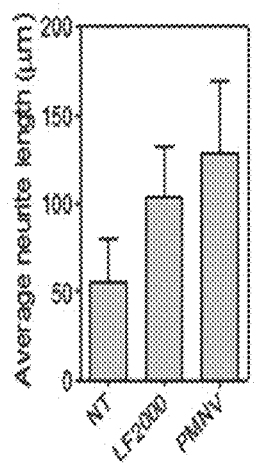

Consequently, as shown in FIGS. 15 and 16, it can be confirmed that the REST expression was considerably lower than the control, and similar to the group using LF 2000 by using the gene carrier (PMNV) of the present invention (refer to FIG. 15), and an enhanced neuronal differentiation potency of hfNSCs was confirmed by inhibition of the REST expression by confirming the decrease in Nestin and GFAP expression and the increase in olig2, Tuj1 and MAP2 expression (refer to FIG. 16). In addition, by the result of measuring the change in neurite length of the hfNSCs, as shown in FIG. 17, it can be confirmed that, when the gene carrier of the present invention is used, compared to the control and the group using LF 2000, the neurite length was considerably increased. From the above result, it can be seen that the technique of the present invention can promote the differentiation into neuronal cells from human neuronal stem cells.

3-4. Analysis of siRNA Delivery Efficiency of Gene Carrier Using hADSCs

In this exemplary embodiment, uniform-sized nanovesicles were prepared by the same method as shown in Example 1-1 using hADSCs instead of a HEK-293 cell line. Afterward, following the preparation of gene carrier by inserting GAPDH siRNA into the nanovesicles, the gene carrier was delivered to the hADSCs, the decrease in GAPDH expression and cytotoxicity were evaluated, and the GAPDH expression was measured as a relative expression ratio with respect to an ACTB gene. Meanwhile, a group to which siRNAs are not delivered (NT) was used as a control, and a group currently using exosomes (Exo) and a group using HEK-293 cell line-derived nanovesicles (HEK293-derived) were used as comparative groups.

Figure 18A:
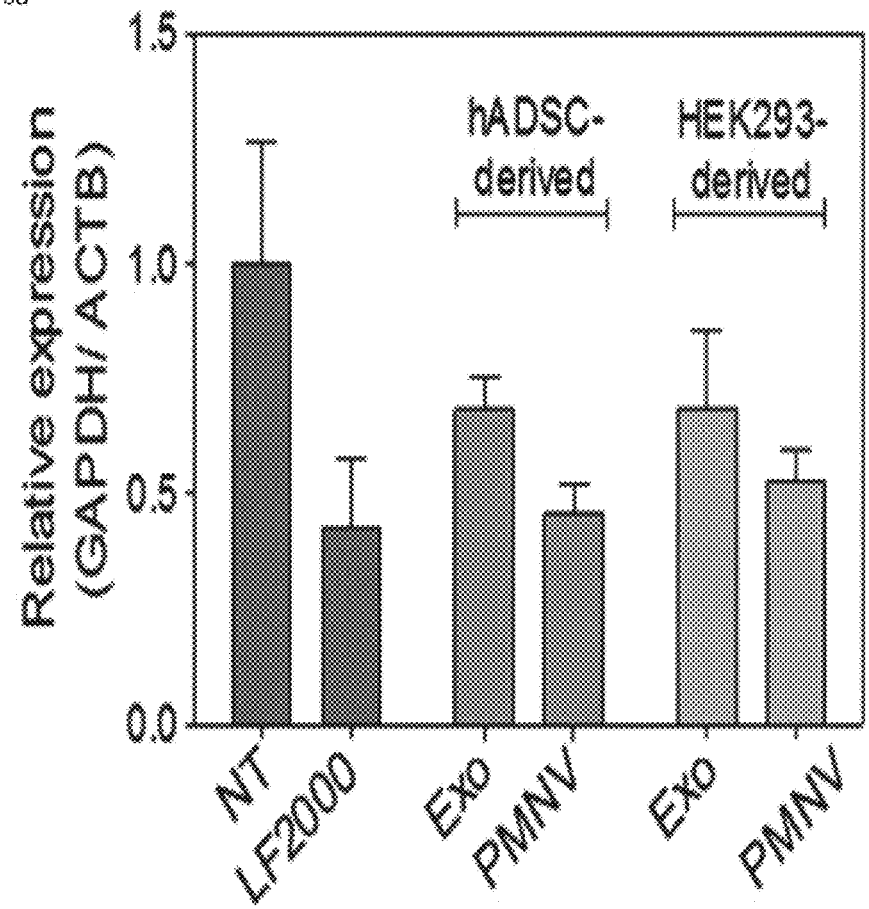
FIG. 18 shows the results of (a) quantifying GAPDH expression and (b) evaluating cytotoxicity after GAPDH siRNAs are delivered to hADSCs using hADSC-derived nanovesicles.
Figure 18B:
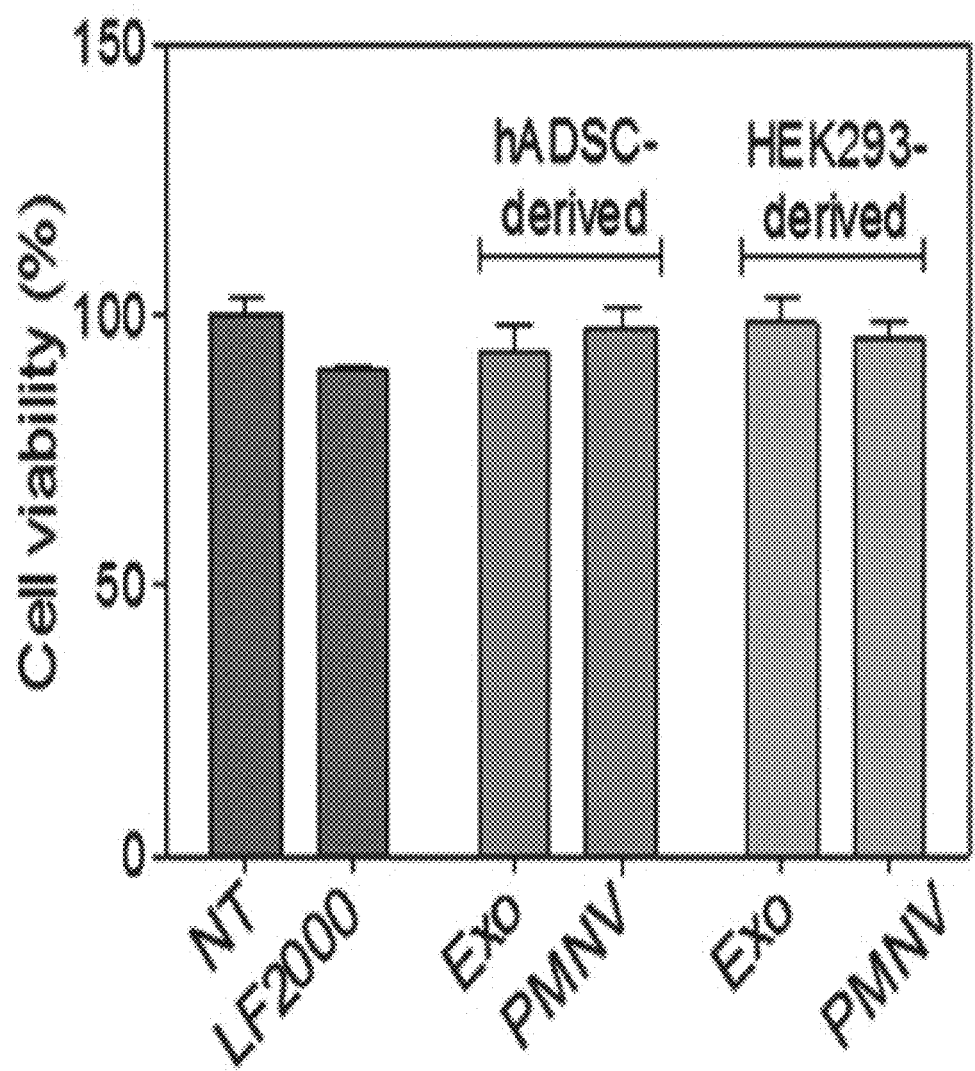

Consequently, as shown in FIG. 18, it can be confirmed that, even when human adipose-derived stem cells were used, as in the case of using the HEK-293 cell line, GAPDH expression was further reduced and cytotoxicity was lower than the group using exosomes. From this result, it can be seen that the gene carrier of the present invention can be prepared using various cells, as well as the HEK-293 cell line.

Experimental Example 4. Enhancement in Delivery Efficiency According to Introduction of Targeting Ligand Based on the assumption that in pluripotent stem cells such as hiPSCs or human embryonic stem cells (hESCs), E-cadherin can be highly expressed, and an E-cadherin-E-cadherin interaction can promote introduction into the cells, the inventors prepared a gene carrier in which E-cadherin, which is a targeting ligand, was expressed by the same method as shown in Preparation Example 1-1, following overexpression of E-cadherin in the HEK-293 cells.

First, the E-cadherin expression in the gene carrier (PMNC-Ecad) of the present invention was confirmed by western blotting, and after Cy5-labeled siRNAs were delivered to hiPSCs using the gene carrier, an intracellular fluorescence intensity thereof was measured. In addition, in the hiPSC and hADSC cells, the decrease in GAPDH expression according to the delivery of GAPDH siRNAs was measured as a relative expression ratio with respect to an ACTB gene, and to define a mechanism of introducing the gene carrier (PMNC-Ecad) into cells, the gene carrier stained with a Dil dye was treated to cells in which clathrin-mediated endocytosis was inhibited by K+ depletion or clathrin heavy chain (CHC) siRNA treatment, or cells in which macropinocytosis was inhibited by treatment of ethyl isopropyl amiloride (EIPA) and an LY294002 compound, and then intracellular uptake was evaluated. Meanwhile, a group to which siRNAs were not delivered (NT) was used as a control, and a nanovesicle (PMNV) in which E-cadherin was not expressed or LF 2000 was used as a comparative group.

Figure 19A:
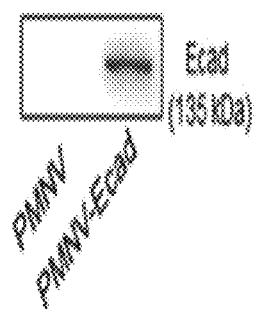
FIG. 19 shows the results of (a) confirming E-cadherin expression by western blotting and (b) confirming introduction of E-cadherin into human induced pluripotent stem cells (hiPSCs) by fluorescence microscopy in the E-cadherin-introduced gene carrier of the present invention.
Figure 19B:
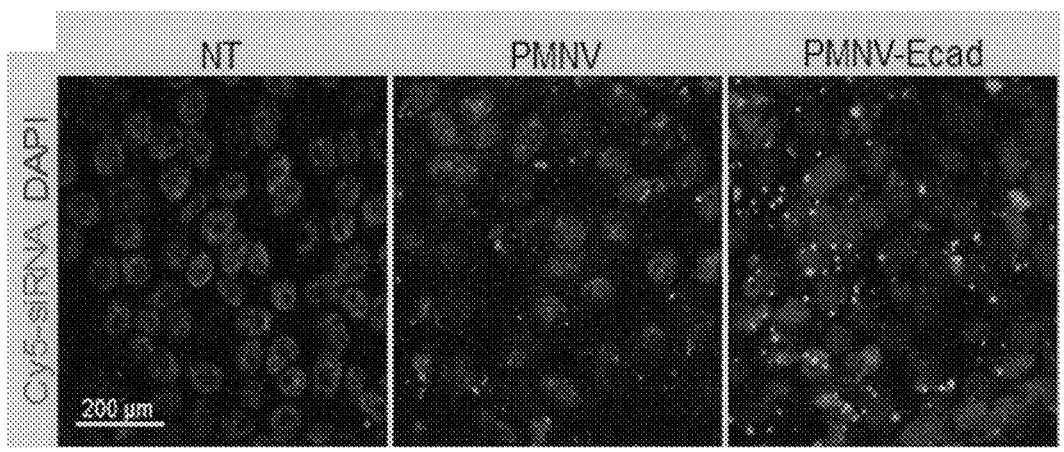
Figure 20A:
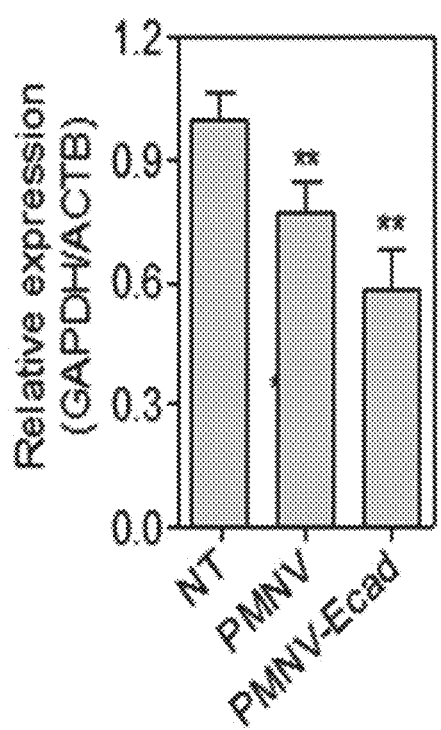
FIG. 20 shows a result of quantifying GAPDH expression after GAPDH siRNAs are delivered to (a) hiPSCs or (b) to hADSCs using the E-cadherin-introduced gene carrier of the present invention.
Figure 20B:
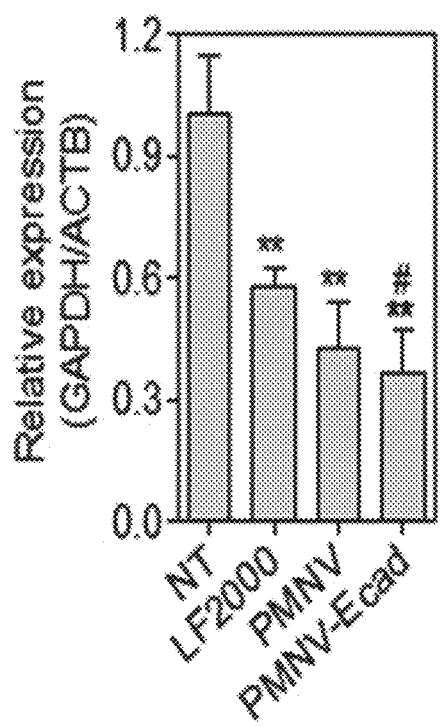
Figure 21A:
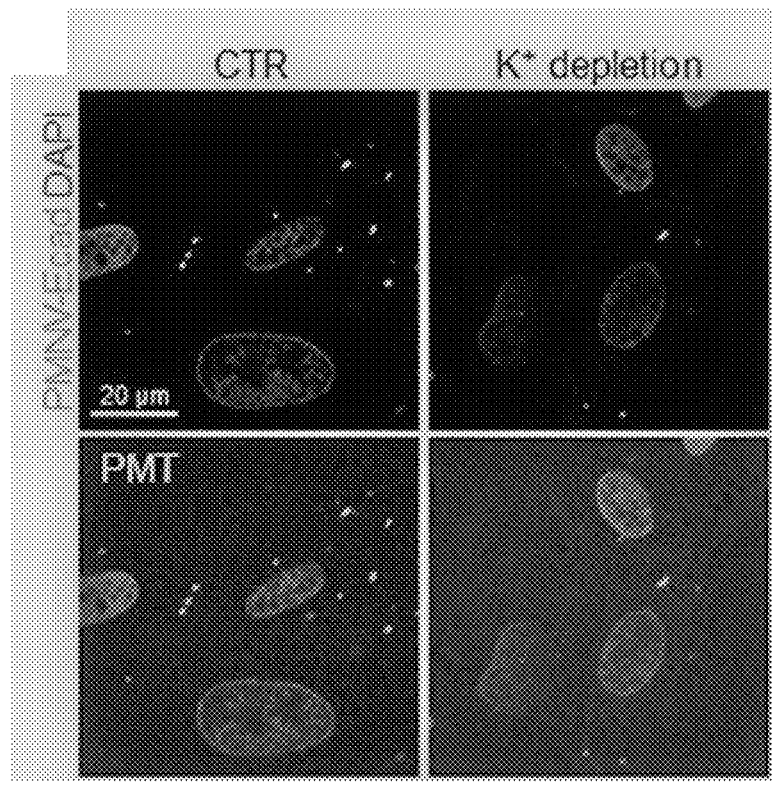
FIG. 21 shows (a) a fluorescent microscopic result, and (b) a quantification result for intracellular uptake, and (c) a quantification result for intracellular uptake after K+ depleted cells are treated with the gene carrier of the present invention stained with a Dil dye.
Figure 21B:
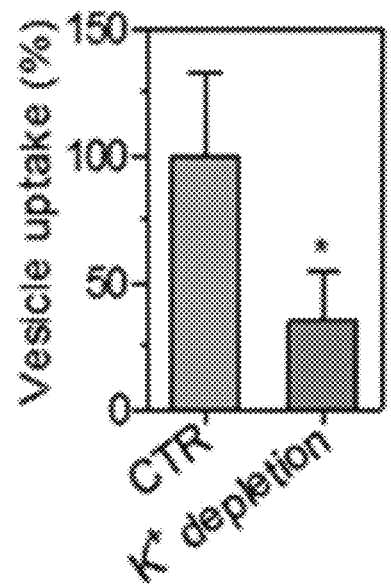
Figure 21C:
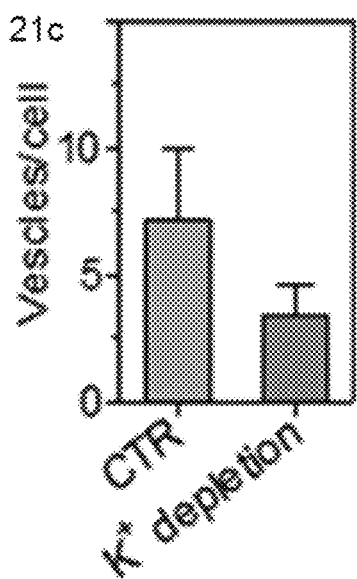
Figure 22A:
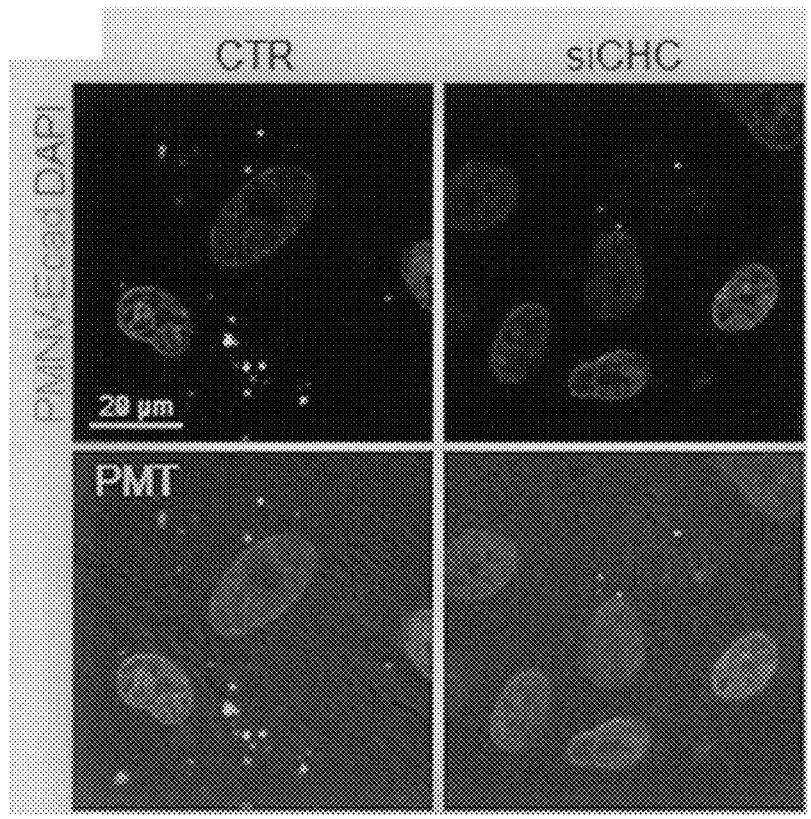
FIG. 22 shows (a) a result of observation by fluorescent microscopy, and (b) a quantification result for intracellular uptake, and (c) a quantification result for intracellular uptake after CHC siRNA-treated cells are treated with the gene carrier of the present invention stained with a Dil dye.
Figure 22B:
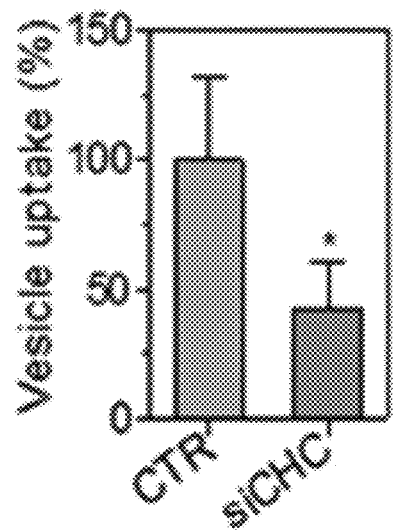
Figure 22C:
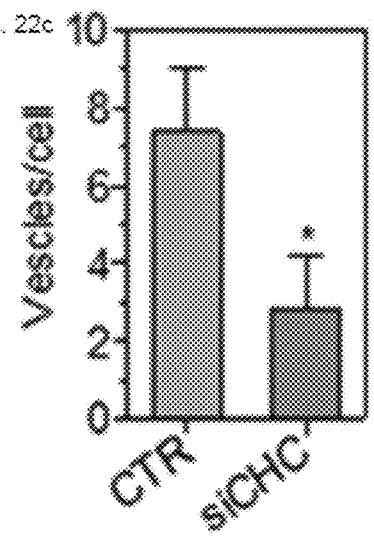
Figure 23A:
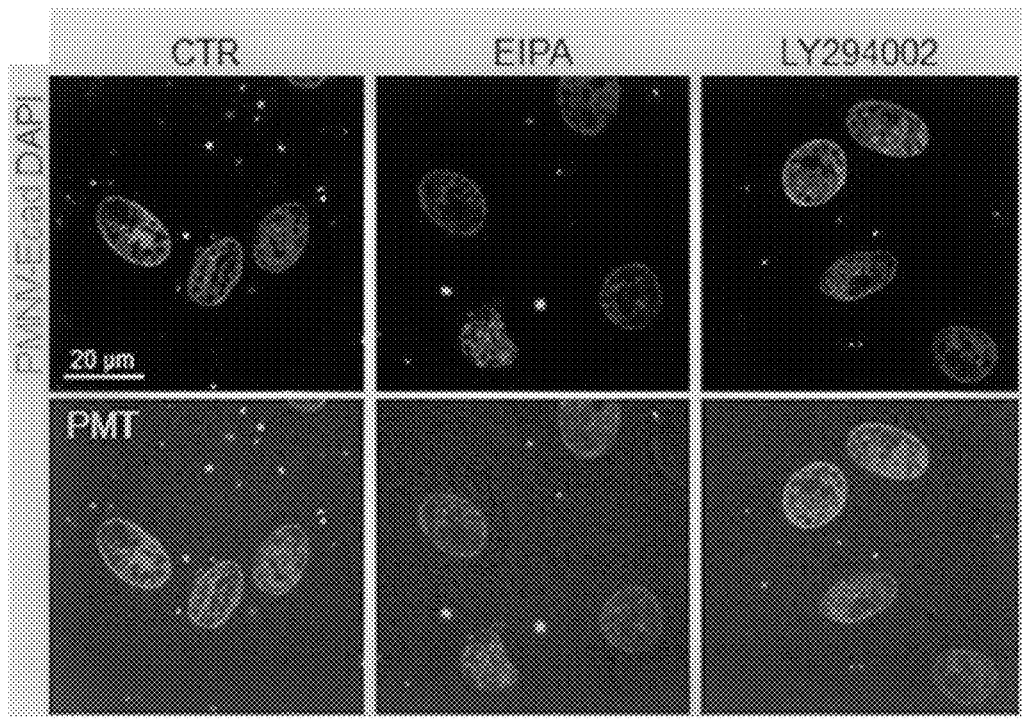
FIG. 23 shows (a) a result of observation by fluorescent microscopy, and (b) a quantification result for intracellular uptake, and (c) a quantification result for intracellular uptake after EIPA or LY294002 compound-treated cells are treated with the gene carrier of the present invention stained with a Dil dye.
Figure 23B:
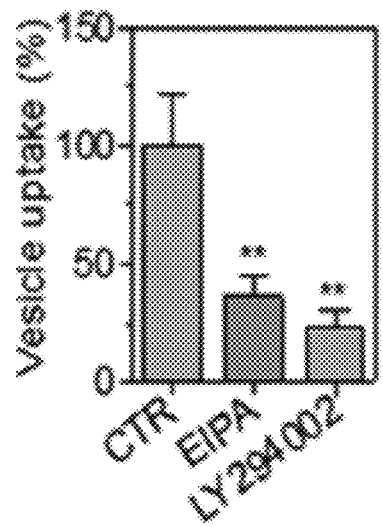
Figure 23C:
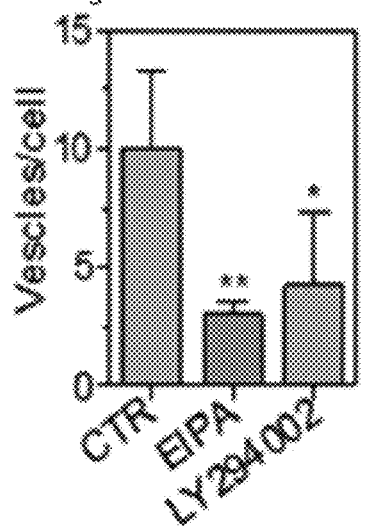

Consequently, as shown in FIG. 19, it can be seen that E-cadherin, which is a targeting ligand, can be easily introduced into the surface of the gene carrier using E-cadherin-overexpressing HEK-293 cells (refer to FIG. 19A), and thus it can be confirmed that a large quantity of siRNA can be delivered into the hiPSCs (refer to FIG. 19B). In addition, after the GAPDH siRNAs were delivered to the hiPSCs and hADSCs, as a result of the quantitative evaluation for the decrease in GAPDH expression, as shown in FIG. 20, when the gene carrier of the present invention was used in both types of cells, compared to the control, and the group using PMNV or LF 2000, it can be confirmed that the reduction ratio of the GAPDH expression was considerably increased. In addition, as shown in FIGS. 21 to 23, it can be seen that the uptake of the nanovesicles were considerably reduced in all three types of cells in which specific mechanisms were blocked, which indicates that clathrin-mediated endocytosis and macropinocytosis serve as the main mechanisms in a process of internalizing the gene carrier of the present invention in the cells.

Experimental Example 5. In Vivo Analysis of siRNA Delivery Efficiency

Hypercholesterolemia causes major cardiovascular diseases including atherosclerosis and coronary heart disease (CHD), etc., and its main cause is high expression of APOB present in a large quantity in liver tissue. In this exemplary embodiment, the APOB siRNA-inserted gene carrier of the present invention was administered to a mouse animal model, and a change in the body caused thereby was observed.

5-1. Live Imaging and Distribution of Gene Carrier

After fluorescence material-labeled APOB siRNA were administered into the caudal vein of the mouse animal model using the gene carrier of the present invention, live imaging and total body fluorescence intensity were measured over time (15 min and 150 min), and the main organs (the heart, lung, liver, kidney, and spleen) were extracted from the mouse to evaluate siRNA distribution per organ. Meanwhile, a group to which siRNAs were not delivered (NT) was used as a control.

Consequently, as shown in FIG. 24, it can be confirmed that 15 minutes after the administration of the gene carrier, siRNA were broadly distributed to the whole body, whereas 150 minutes after the administration, most siRNA were accumulated in the liver (refer to FIG. 24A). It can be confirmed that, although time elapsed, the fluorescence intensity was maintained at a high level (refer to FIG. 24B). In addition, as a result of measuring the siRNA quantity in the extracted organs, high intensities of fluorescence were measured in the liver and the kidney (refer to FIGS. 24C and 24D).

5-2. Decrease in Expression by Gene Carrier

After APOB siRNA were administered into a mouse animal model by the same method as described in Experimental Example 4-1 using the gene carrier of the present invention, the decrease in APOB expression in liver tissue due to the administration was measured as a relative expression ratio with respect to a GAPDH gene. A PBS buffer-injected group (PBS) was used as a control, and a scrambled siRNA (siSCR)-inserted group was used as a comparative group.

Figure 25:
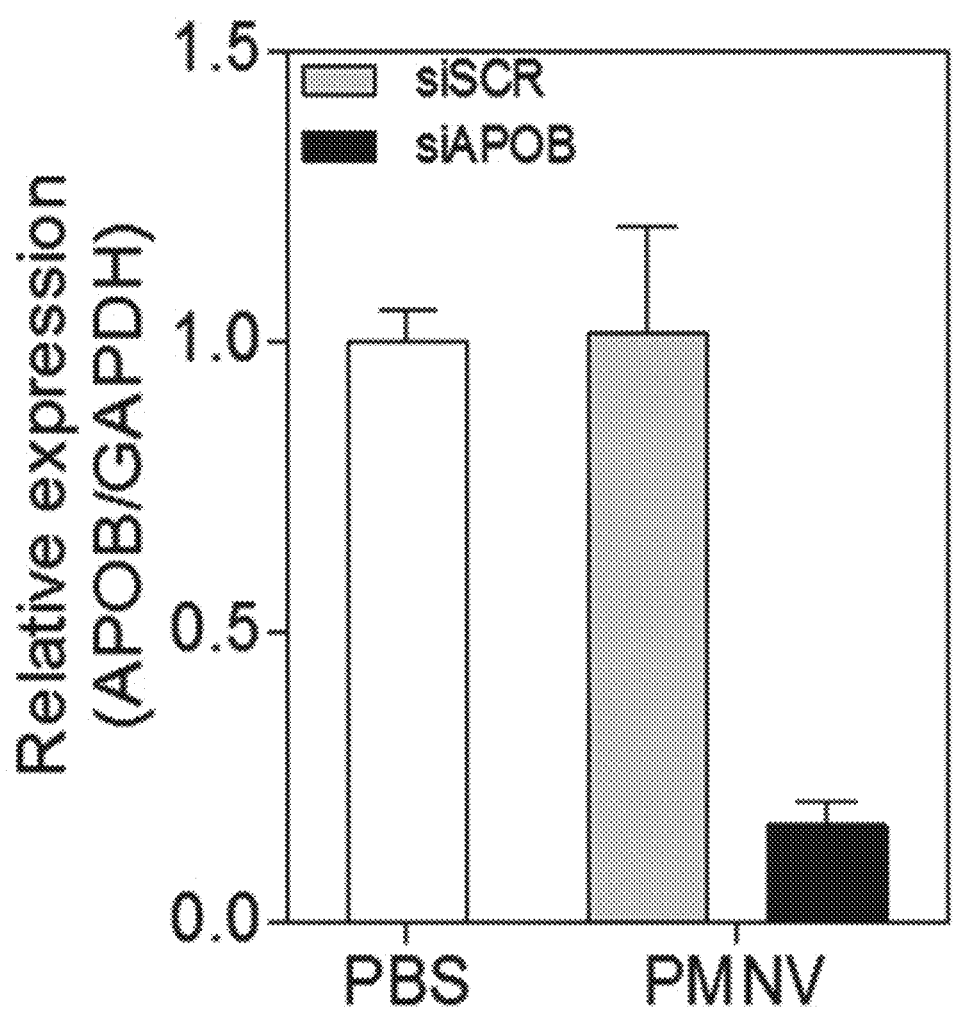
FIG. 25 shows a result of quantifying APOB expression in liver tissue after APOB siRNAs are delivered to a mouse animal model using the gene carrier of the present invention.

Consequently, as shown in FIG. 25, the control and the scrambled siRNA-inserted group did not show a change in APOB expression in liver tissue, whereas when the gene carrier of the present invention (PMNV) was used, it was confirmed that the APOB expression was considerably decreased. Accordingly, it can be seen that the gene carrier of the present invention effectively exhibited its function even in vivo.

5-3. Evaluation of In Vivo Toxicity of Gene Carrier

The gene carrier prepared by inserting scrambled siRNA into the nanovesicles extracted from mouse-derived dermal cells was administered to a mouse, and the change in blood concentrations of aspartate aminotransferase (AST) and alanine transaminase (ALT) over time (12 hours before the administration, 12 hours or 24 hours after the administration) was measured to evaluate whether in vivo toxicity was caused. A PBS buffer-injected group (PBS) was used as a control.

Consequently, as shown in FIG. 26, there was no significant change in concentrations of AST and ALT before and after the administration of the gene carrier (PMNV/siRNA), and there was no significant difference from the control, either, and thus inherent in vivo toxicity of the gene carrier of the present invention was not observed.

Experimental Example 6. Intracellular DNA Delivery by Gene Carrier of the Present Invention In this exemplary embodiment, after being inserted into the nanovesicle prepared in Preparation Example 1-2, an EGFP plasmid was delivered to a HeLa cell line and hADSCs, and an increase in EGFP expression caused thereby was observed by fluorescence microscopy. An LF 2000-EGFP and luciferase-inserted group (PMNV-Luc) were used as controls for the HeLa cell line, and a non-transformed group (NT) and a PaMNV-Luc group were used as controls for hADSCs.

Figure 27A:
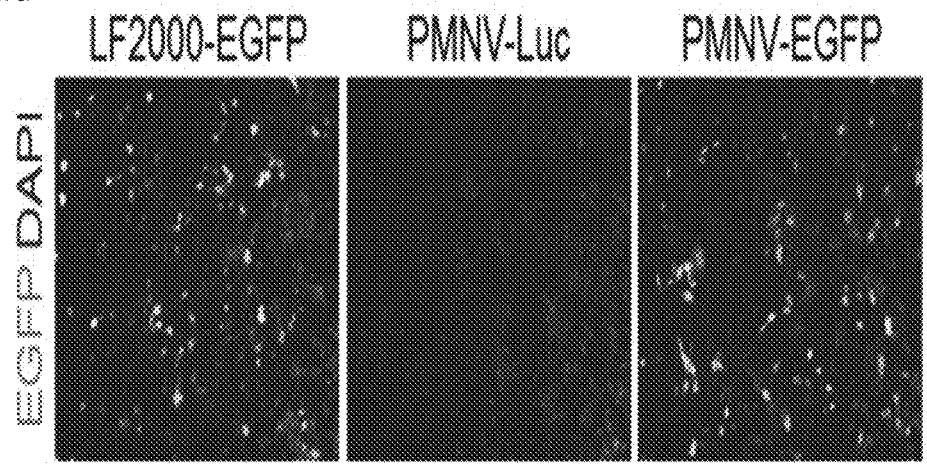
FIG. 27 shows a fluorescent microscopic result of observing EGFP expression, by fluorescent microscopy, after a EGFP plasmid is delivered to (a) a HeLa cell line or (b) hADSCs using the gene carrier of the present invention.
Figure 27B:
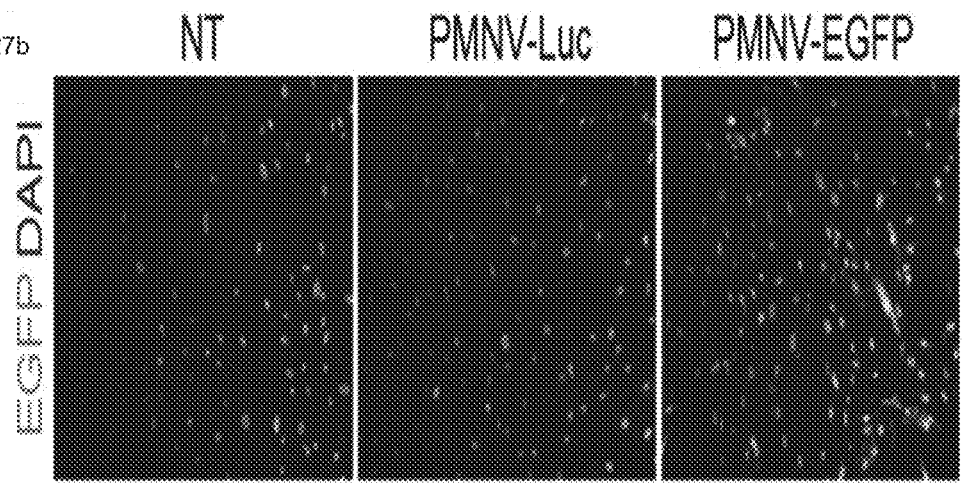

Consequently, as shown in FIG. 27, it can be confirmed that, when the gene carrier of the present invention was used, the EGFP expression was increased in both of the HeLa cell line and the hADSCs, and from this result, it can be seen that the gene carrier of the present invention can also be applied to DNA delivery.

A method for preparing a gene carrier according to the present invention includes inserting a gene into nanovesicles which are artificially outbudded from a plasma membrane, and the gene carrier prepared thereby can be used as a core technique in the gene or cell therapeutic agent field because it has excellent delivery efficiency to a target organ and cells, is able to induce the long-term regulation of gene expression, and facilitates mass production due to a simple production process. In addition, since a gene carrier optimized for a patient using a patient's own cells can be prepared using the method of the present invention, it can be applied to personalized gene therapy.

It would be understood by those of ordinary skill in the art that the above description of the present invention is exemplary, and the exemplary embodiments disclosed herein can be easily modified into other specific forms without departing from the technical spirit or essential features of the present invention. Therefore, the exemplary embodiments described above should be interpreted as illustrative and not limited in any aspect.

What is claimed is:

1. A method for preparing a RNA carrier, comprising:
(a) preparing nanovesicles by extruding a suspension containing vesicles outbudded from cells; and
(b) inserting a RNA into the prepared nanovesicles,
wherein the vesicles are outbudded by being cultured in a buffer solution containing paraformaldehyde (PFA) and dithiothreitol (DTT), and
the RNA is selected from the group consisting of mRNA, tRNA, rRNA, siRNA, and miRNA.

2. The method of claim 1, wherein, before Step (a), overexpressing a targeting ligand on the surface of cells.

3. The method of claim 1, wherein the cells are selected from the group consisting of human embryonic kidney-293 (HEK-293) cells, human adipose-derived stem cells, bone marrow stem cells, dermal cells, and blood cells.

4. The method of claim 1, wherein the buffer solution contains 25 to 50 mM PFA and 1 to 5 mM DTT.

5. A gene carrier comprising:
(a) nanovesicles prepared by extruding a suspension containing vesicles outbudded from cells; and
(b) a nucleotide inserted into the nanovesicles,
wherein the vesicles are outbudded by being cultured in a buffer solution containing paraformaldehyde (PFA) and dithiothreitol (DTT),
the cells overexpress E-cadherin, and
the nucleotide is selected from the group consisting of mRNA, tRNA, rRNA, siRNA, and miRNA.

6. A method for preparing a DNA carrier, comprising:
(a) preparing microvesicles by centrifuging a suspension containing vesicles outbudded from cells;
(b) treating the microvesicles with a surfactant and a DNA to insert the nucleotide in the microvesicles; and
(c) preparing nanovesicles by extruding a suspension containing the nucleotide-inserted microvesicles,
wherein the vesicles are outbudded by being cultured in a buffer solution containing paraformaldehyde (PFA) and dithiothreitol (DTT), and
the DNA is selected from the group consisting of gDNA, pDNA, and cDNA.

7. The method of claim 6, wherein before Step (a), overexpressing a targeting ligand on the surface of cells.

8. The method of claim 6, wherein the cells are selected from the group consisting of human embryonic kidney-293 (HEK-293) cells, human adipose-derived stem cells, bone marrow stem cells, dermal cells, and blood cells.

9. The method of claim 6, wherein the buffer solution contains 25 to 50 mM PFA and 1 to 5 mM DTT.

10. The method of claim 6, wherein the surfactant is Triton X-100.

* * * * *